US007041479B2

(12) United States Patent
Swartz et al.

(10) Patent No.: US 7,041,479 B2
(45) Date of Patent: *May 9, 2006

(54) ENHANCED IN VITRO SYNTHESIS OF ACTIVE PROTEINS CONTAINING DISULFIDE BONDS

(75) Inventors: James Robert Swartz, Menlo Park, CA (US); Dong-Myung Kim, Walnut Creek, CA (US)

(73) Assignee: The Board of Trustess of the Leland Stanford Junior University, Palo Alto, CA (US)

( * ) Notice: Subject to any disclaimer, the term of this patent is extended or adjusted under 35 U.S.C. 154(b) by 396 days.

This patent is subject to a terminal disclaimer.

(21) Appl. No.: 10/404,599

(22) Filed: Mar. 31, 2003

(65) Prior Publication Data

US 2004/0038332 A1    Feb. 26, 2004

Related U.S. Application Data

(63) Continuation-in-part of application No. 09/948,052, filed on Sep. 5, 2001, now Pat. No. 6,548,276.

(60) Provisional application No. 60/230,381, filed on Sep. 6, 2000.

(51) Int. Cl.
*C12P 21/00* (2006.01)
*C12Q 1/02* (2006.01)

(52) U.S. Cl. .................. 435/70.1; 435/69.1; 435/25; 435/189; 435/215; 435/243; 530/350

(58) Field of Classification Search ............. 435/70.1, 435/69.1, 25, 189, 215, 243; 530/350
See application file for complete search history.

(56) References Cited

U.S. PATENT DOCUMENTS 6,548,276 B1 *  4/2003  Swartz et al. .............. 435/70.1

OTHER PUBLICATIONS

Bukau, B. et al., *The Hsp70 and Hsp60 Chaperone Machines*, Review, Cell, A Scientific Breakthrough, vol. 92, 351-366, Cell Press (Feb. 1998).
Bessette, P.H. et al., *Efficient folding of proteins with multiple disulfide bonds in Escherichia coli cytoplasm*, PNAS, vol. 96, No. 24, 13703-13708 (Nov. 23, 1999).

Kim, D.M. et al., *Prolonging Cell-Free Protein Synthesis by Selective Reagent Additions*, Biotechnol Prog. May-Jun. 2000;16(3):385-90 (2000).
Kim, D.M. et al., *Prolonging Cell-Free Protein Synthesis with a Novel ATP Regeneration System*, Biotechnology and Bioengineering, vol. 66, No. 3, pp. 180-188 (1999).
Kim, D.M. et al., *A highly efficient cell-free protein synthesis system fro Escherichia coli*, Eur. J. Biochem. 239, pp. 881-886, FEBS (1996).
Missiakas, D. et al., *Protein Folding in the Bacterial Periplasm*, Minireview, Journal of Bacteriology, vol. 179, No. 8, p. 2465-2471, American Society for Microbiology (Apr. 1997).
Noren, C.J. et al., *A General Method for Site-Specific Incorporation of Unnatural Amino Acids into Proteins*, Science, Research Articles, vol. 244, pp. 182-188 (Apr. 14, 1989).
Richardson, A., et al., *The ins and outs of a molecular chaperone machine*, Reviews, TIBS, pp. 138-143, Elsevier Science Ltd. (Apr. 23, 1998).
Qiu, J. et al., *Expression of Active Human Tissue-Type Plasminogen Activator in Escherichia coli*, Applied and Environmental Microbiology, vol. 64, No. 12, pp. 4891-4896, 0099-2240, American Society for Microbiology (Dec. 1998).
Kim, Dong-Myung et al., Efficient Production of a Bioactive, Multiple Disulfide-Bonded Protein Using Modified Extracts of *Escherichia coli*, 2003, Wiley Periodicals, Inc., published online in Wiley InterScience (ww.interscience.wiley.com), Biotechnology and Bioengineering, vol. 85 No. 2, p. 122-129 (Jan. 2004).
Ryabova, Lyubov A., *Functional antibody production using cell-free translation: Effects of protein disulfide isomerase and chaperones*, Nature Biotechnology, Jan. 1997, vol. 15, No. 1, p. 79-84.

* cited by examiner

*Primary Examiner*—Chih-Min Kam
(74) *Attorney, Agent, or Firm*—Pamela J. Sherwood; Bozicevic, Field & Francis LLP

(57) ABSTRACT

Compositions and methods are provided for the enhanced in vitro synthesis of polypeptides containing disulfide bonds. In order to improve the performance of in vitro protein synthesis reactions, pre-treatment and redox buffering of the reaction mix is performed in order to optimize the redox potential. Exogenous enzymes that enhance protein folding and disulfide bond formation may also be added to the reaction.

23 Claims, 12 Drawing Sheets

FIGURE 7A
FIGURE 7B
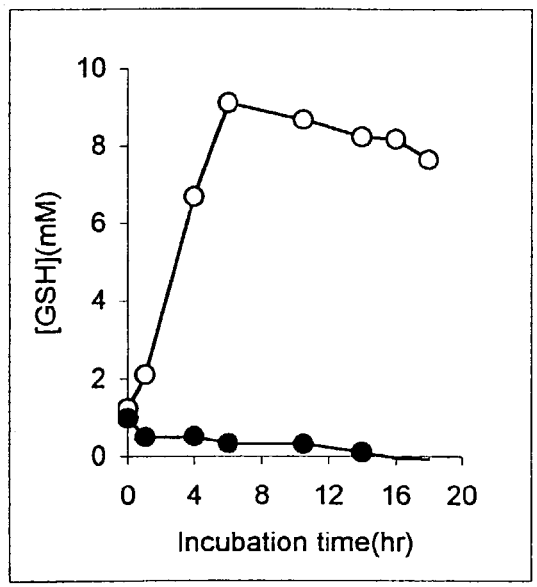
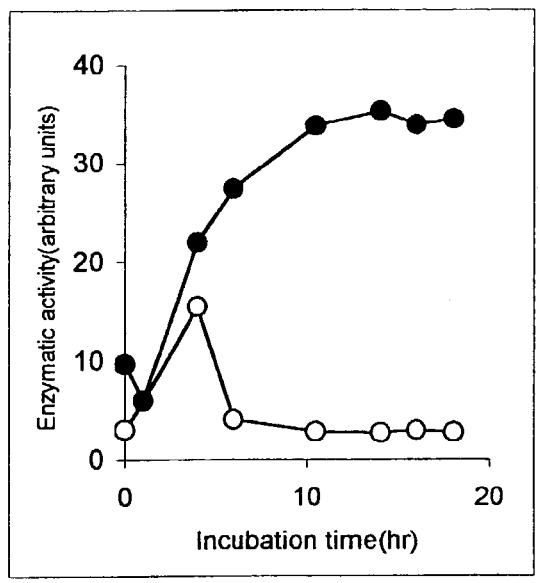

ENHANCED IN VITRO SYNTHESIS OF ACTIVE PROTEINS CONTAINING DISULFIDE BONDS

BACKGROUND OF THE INVENTION

*Escherichia coli* is a widely used organism for the expression of heterologous proteins. It easily grows to a high cell density on inexpensive substrates to provide excellent volumetric and economic productivities. Well established genetic techniques and various expression vectors further justify the use of *Escherichia coli* as a production host. However, a high rate of protein synthesis is necessary, but by no means sufficient, for the efficient production of active biomolecules. In order to be biologically active, the polypeptide chain has to fold into the correct native three-dimensional structure, including the appropriate formation of disulfide bonds.

In many cases, the recombinant polypeptides have been found to be sequestered within large retractile aggregates known as inclusion bodies. Active proteins can be recovered from inclusion bodies through a cycle of denaturant-induced solubilization of the aggregates followed by removal of the denaturant under conditions that favor refolding. But although the formation of inclusion bodies can sometimes ease the purification of expressed proteins; in most occasions, refolding of the aggregated proteins remains a challenge.

Various attempts have been made to improve the folding of heterologous proteins in the bacterial cytoplasm. In addition to the traditional methods, including lowering the temperature of the culture, increasing knowledge of the mechanism and effectors of protein folding has enabled new approaches to solve the problem of aggregation.

Studies in vitro have demonstrated that, for the vast majority of polypeptides, folding is a spontaneous process directed by the amino acid sequence and the solvent conditions. Yet, even though the native state is thermodynamically favored, the time-scale for folding can vary from milliseconds to days. Kinetic barriers are introduced, for example, by the need for alignment of subunits and sub-domains. And particularly with eukaryotic proteins, covalent reactions must take place for the correctly folded protein to form. The latter types of reaction include disulfide bond formation, cis/trans isomerization of the polypeptide chain around proline peptide bonds, preprotein processing and the ligation of prosthetic groups. These kinetic limitations result in the accumulation of partially folded intermediates, that contain exposed hydrophobic 'sticky' surfaces which promote self-association and formation of aggregates.

Expression of mammalian proteins is more complicated than bacterial proteins because most of them require intramolecular disulfide bonds for their activity. Thus additional effectors such as foldases and proper redox potential are required to achieve their native structures. Even though the periplasmic space of *Escherichia coli* provides an oxidizing environment as well as folding proteins such as DsbA, B, C, and D; in many cases, simple secretion of complex proteins into the periplasmic space is not sufficient to form correct disulfide bonds.

Accessory proteins known as foldases and chaperones have been found to assist in the proper folding of proteins in vivo. Foldases have a catalytic activity that serves to accelerate rate-limiting covalent steps in folding. Chaperones, on the other hand, perform many functions, the most important of which is to provide an environment for nascent proteins to fold without the competing process of self-association. In addition to the well-characterized molecular chaperones, such as GroEL and DnaK proteins, a number of additional cytoplasmic proteins have been identified to affect the folding of heterologous proteins.

Following the discovery of numerous bacterial or eukaryotic foldases and their specific roles in the oxidation and isomerization of disulfide bonds, many attempts have been made to use those proteins in the periplasmic space or even in the cytoplasm of *Escherichia coli* (see, for example, Bessette et al. (1999)). The co-expression of molecular chaperones has been shown to partially solve the problem of inclusion body formation in the expression of certain recombinant proteins (see, for example, Richardson et al. (1998) *Trends Biochem. Sci.* 23:138–143; and Bukau et al. (1998) *Cell* 92:351–366).

However, the effect of molecular chaperones is rather product-specific and the co-expression of each molecular chaperone with the target proteins is often cumbersome. Moreover, in some cases, the expression of a molecular chaperone is harmful or even detrimental to cell growth. Despite the recent advances, the expression of properly folded mammalian proteins in *Escherichia coli* still remains as a great challenge. This is mainly due to the difficulties in the control of the key parameters for disulfide bond formation including the redox potential inside the cells.

For several decades, in vitro protein synthesis has served as an effective tool for lab-scale expression of cloned or synthesized genetic materials. In recent years, in vitro protein synthesis has been considered as an alternative to conventional recombinant DNA technology, because of disadvantages associated with cellular expression. In vivo, proteins can be degraded or modified by several enzymes synthesized with the growth of the cell, and, after synthesis, may be modified by post-translational processing, such as glycosylation, deamidation or oxidation. In addition, many products inhibit metabolic processes and their synthesis must compete with other cellular processes required to reproduce the cell and to protect its genetic information.

Because it is essentially free from cellular regulation of gene expression, in vitro protein synthesis has advantages in the production of cytotoxic, unstable, or insoluble proteins. The over-production of protein beyond a predetermined concentration can be difficult to obtain in vivo, because the expression levels are regulated by the concentration of product. The concentration of protein accumulated in the cell generally affects the viability of the cell, so that over-production of the desired protein is difficult to obtain. In an isolation and purification process, many kinds of protein are insoluble or unstable, and are either degraded by intracellular proteases or aggregate in inclusion bodies, so that the loss rate is high.

In vitro synthesis circumvents many of these problems (see Kim and Swartz (1999) *Biotechnol. Bioeng.* 66:180–188; and Kim and Swartz (2000) *Biotechnol. Prog.* 16:385–390). Also, through simultaneous and rapid expression of various proteins in a multiplexed configuration, this technology can provide a valuable tool for development of combinatorial arrays for research, and for screening of proteins. In addition, various kinds of unnatural amino acids can be efficiently incorporated into proteins for specific purposes (Noren et al. (1989) *Science* 244:182–188).

Unlike in vivo gene expression, cell-free protein synthesis uses isolated translational machinery instead of entire cells. As a result, this method eliminates the requirement to maintain cell physiology and allows direct control of various parameters to optimize the synthesis/folding of target proteins. Of particular interest is the problem of cell-free synthesis of biologically active mammalian proteins having multiple disulfide bonds. The present invention addresses the coupled synthesis and folding of mammalian proteins through the control of redox potential during protein synthesis.

SUMMARY OF THE INVENTION

Compositions and methods are provided for the enhanced in vitro synthesis of protein molecules, by optimizing the redox conditions in the reaction mix. In one embodiment of the invention, a redox buffer is included in the reaction mix to maintain the appropriate oxidizing environment for the formation of proper disulfide bonds, for example by the inclusion of glutathione in an appropriate ratio of oxidized to reduced forms.

The reaction mix is preferably further modified to decrease the activity of molecules in the extract, e.g. endogenous enzymes that have reducing activity. Preferably such molecules are chemically inactivated prior to cell-free protein synthesis, e.g. by treatment of the extracts with iodoacetamide (IAM), or other compounds that irreversibly inactivate free sulfhydryl groups. In one embodiment, a stable redox potential is achieved by treating a cell extract with iodoacetamide and utilizing a mixture of oxidized and reduced glutathione. The presence of endogenous enzymes having reducing activity may be further diminished by the use of extracts prepared from genetically modified cells having inactivating mutations in such enzymes, for example thioredoxin reductase, glutathione reductase, etc. Alternatively, such enzymes can be removed by selective removal from the cell extract during its preparation.

In addition to stabilizing the redox potential of the reaction mix, the in vitro synthesis may be further enhanced by the inclusion of accessory proteins that assist in the proper folding of proteins in vivo. Of particular interest is the inclusion of foldases, proteins with a catalytic activity that serve to accelerate rate-limiting covalent steps in folding, e.g. PDI, dsbC, Skp, etc. Other modifications of interest include performing the reactions in the substantial absence of polyethylene glycol, which may be replaced with, e.g. spermidine, spermine, putrescine, and the like. The temperature at which the reaction takes place may be optimized for the protein, e.g. by reducing the temperature to about 25°, about 30°, about 32°, about 35°, about 37°, and the like.

In one embodiment of the invention, methods are provided for screening in vitro synthesis reaction conditions in order to optimize folding and correct formation of disulfide bonds. A plurality of reactions having a stable redox potential are assayed for synthesis of the active form of a protein containing at least one disulfide bond, i.e. a protein that is correctly folded. The reaction conditions are optimized, for example, by inclusion of foldase protein(s), and for temperature. Reactions conditions may also be optimized by varying the level of compounds that irreversibly inactivate free sulfhydryl groups, and the ratio of oxidized to reduced forms of the redox buffer.

BRIEF DESCRIPTION OF THE DRAWINGS

FIGS. 7A and 7B show time courses of glutathione reduction and enzymatic activity of product in control and IAM treated extracts.

cell-freecell-free

Figure 11:
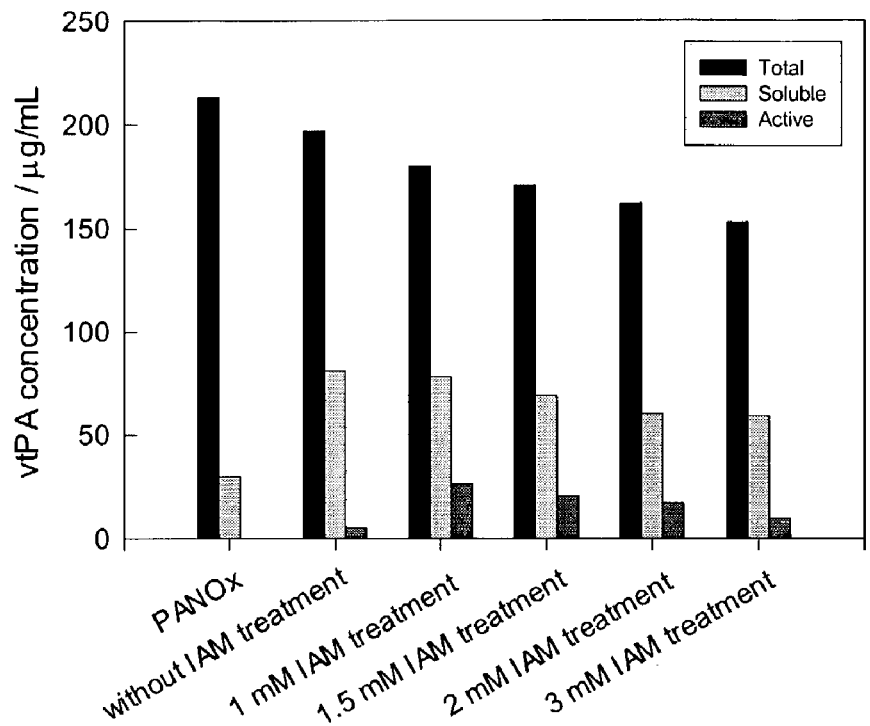

FIG. 11 shows vtPA yields as a function of the iodoacetamide concentration used in the extract pretreatment. The standard cell-free reaction was run as control (PANOx). The cell extracts without IAM pretreatment and with different IAM concentrations during pretreatment was used to express vtPA in the cell-free system. 4 mM GSSG, 1 mM GSH and 75 µg/mL DsbC were present in the cell-free reactions except the control (PANOx) reaction.

Figure 12:
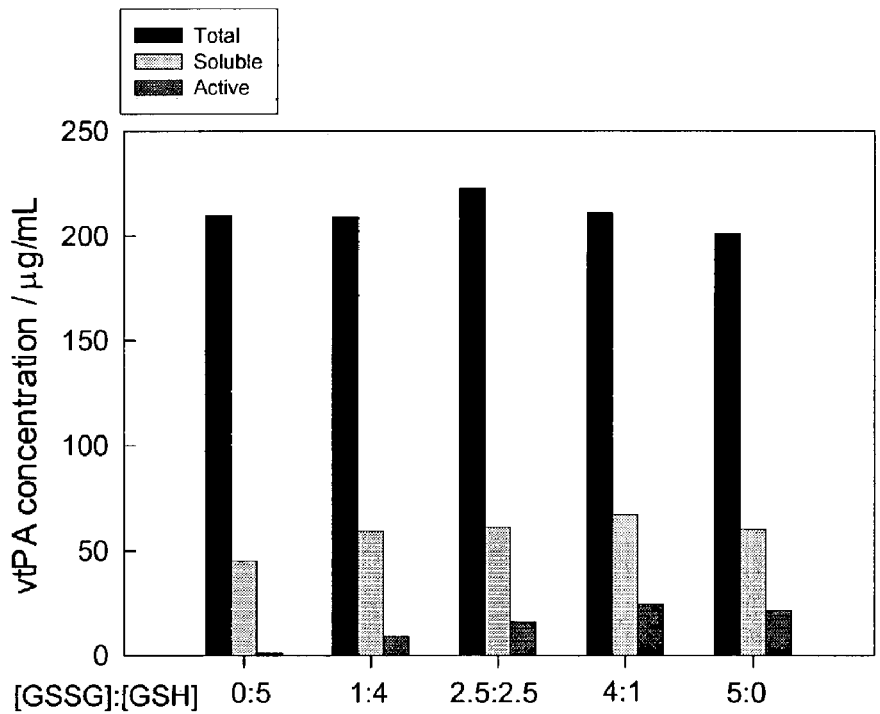

FIG. 12 depicts optimization of the ratio of GSSG and GSH. In the presence of 75 µg/mL DsbC and with 1 mM IAM cell extract pretreatment, the expression of vtPA was determined at different ratios of GSSG and GSH. The total concentration of GSSG plus GSH was 5 mM.

Figure 13:
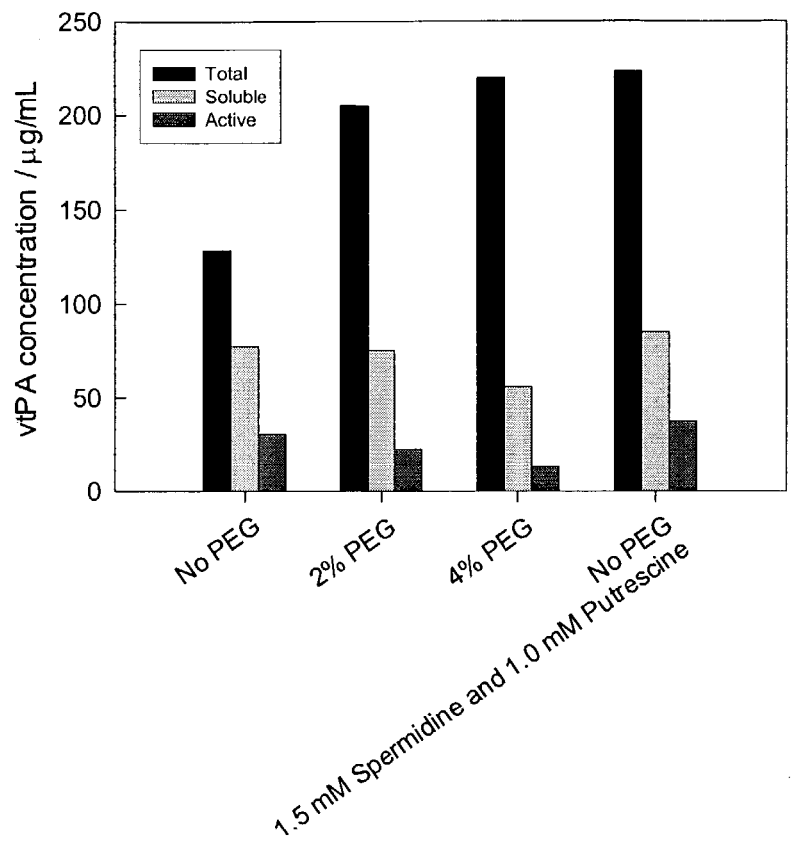

FIG. 13 depicts the effect of PEG, spermidine and putrescine on active vtPA expression in the cell-free system. Different concentrations of PEG were tested for the expression of vtPA in a modified cell-free system (in the presence of 4 mM GSSG, 1 mM GSH, 75 µg/mL DsbC and with 1 mM IAM cell extract pretreatment). vtPA was also expressed in the presence of 1.5 mM spermidine and 1.0 mM putrescine and in the absence of PEG.

Figure 14:
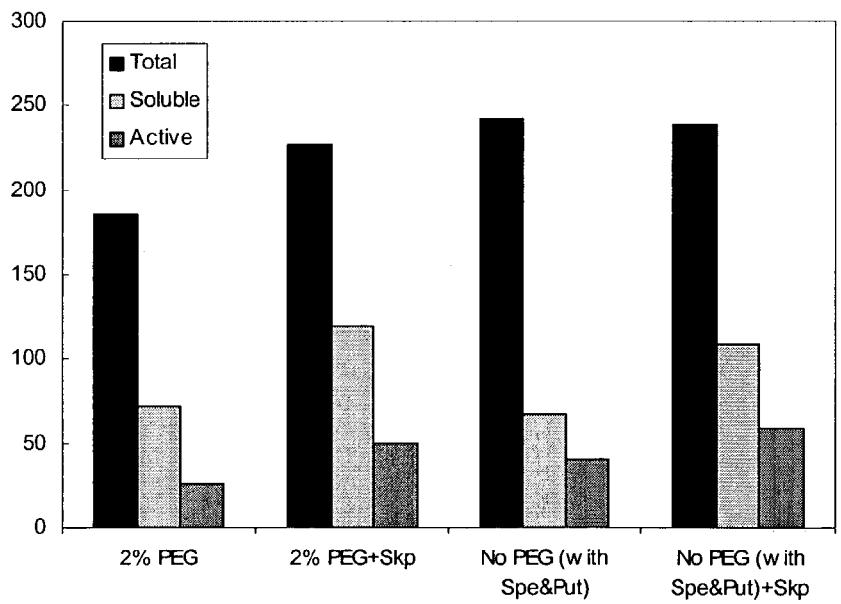

FIG. 14 shows the effect of 300 µg/ml of Skp on soluble and active yield. Under the optimized redox environment (1 mM IAM cell extract pretreatment, 4 mM GSSG and 1 mM GSH) and in the presence of 75 µg/mL DsbC, the effect of Skp on the expression of active vtPA was investigated.

Figure 15:
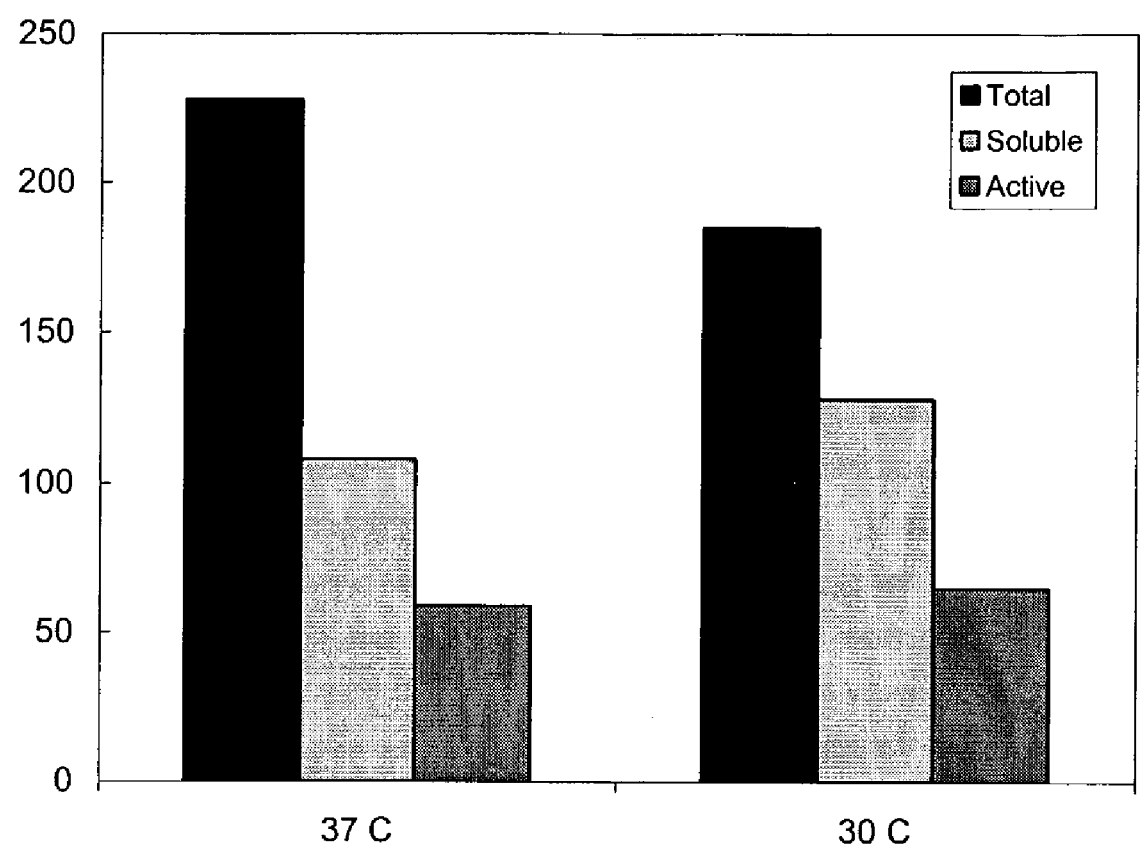

FIG. 15 illustrates protein synthesis as a function of temperature. The cell-free expression of vtPA was conducted at 37° C. and 30° C. in the presence of 4 mM GSSG, 1 mM GSH, 75 µg/mL DsbC, 1.5 mM spermidine, 1.0 mM putrescine and 300 µg/mL Skp and in the absence of PEG.

DETAILED DESCRIPTION OF THE EMBODIMENTS

Compositions and methods are provided for the enhanced in vitro synthesis of biologically active proteins, particularly proteins comprising one or more disulfide bonds. The reaction mix for in vitro protein synthesis is modified to improve protein folding, and formation of disulfide bonds. A redox buffer is included in the reaction mix to maintain the appropriate oxidizing environment, for example by the inclusion of glutathione in an appropriate ratio of oxidized to reduced forms. That redox buffer is further stabilized by inactivating endogenous oxidoreductase reactions. The inclusion of a redox buffer enables the production of bioactive proteins that require the formation of one or more intramolecular disulfide bonds for activity.

In a preferred embodiment, endogenous molecules that reduce the redox buffer are chemically inactivated prior to synthesis, e.g. by treatment of the extracts with compounds such as iodoacetamide (IAM), which irreversibly inactivate free sulfhydryl groups.

In some methods of in vitro protein synthesis, endogenous enzymes are utilized for the generation or replenishment of energy sources used in the reaction (see, for example, co-pending patent application Ser. No. 09/270,814). In some instances, such endogenous enzymes are inactivated by the chemical inactivation step described above, and in that case it may be desirable to replenish these enzymes from an exogenous source, prior to, or concurrent with synthesis. By way of example, if the use of non-traditional secondary energy sources such as early glycolytic intermediates (for example, glucose 6-phosphate) is desired, the activity of glyceraldehyde 3-phosphate dehydrogenase can be restored by any of several methods known in the art.

The presence of endogenous enzymes having reducing activity may be further diminished by the use of extracts prepared from genetically modified cells having inactivating mutations in such enzymes, for example thioredoxin reductase, glutathione reductase, etc.

Alternatively, the enzymes conveying such reducing activity may be diminished by selectively removing them from the cell extract prior to use.

In addition to buffering the redox potential of the reaction mix, the in vitro synthesis may be further enhanced by the inclusion of accessory proteins that assist in the proper folding of proteins in vivo. Of particular interest is the inclusion of foldases, proteins with a catalytic activity that serve to accelerate rate-limiting covalent steps in folding, e.g. PDI, dsbC, etc.

These methods are applicable to continuous, semi-continuous and batch reactions. In the semi-continuous system, even where the endogenous reducing enzymes are not inactivated, the level of oxidation of the redox buffer will recover substantially after an extended incubation. The recovery of an oxidizing environment in the reaction chamber allows the synthesized protein to acquire disulfide bonds and activity. However, the extracts with inactivated oxidoreductases provide more rapid formation of bioactive proteins.

For some synthetic reactions, e.g. multiplexed reactions, it is preferable to use batch rather than a semi-continuous system. For batch synthesis methods, the reaction mix is preferably modified to decrease the activity of molecules in the extract, e.g. endogenous enzymes, that have reducing activity.

Definitions

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this invention belongs unless clearly indicated otherwise.

Folding, as used herein, refers to the three-dimensional structure of polypeptides and proteins or the process of attaining such a structure, where interactions between amino acid residues act to stabilize the structure. While non-covalent interactions are important in determining structure, usually the peptides and proteins of interest will have intra- and/or intermolecular covalent bonds formed by two cysteine residues. For naturally occurring proteins and polypeptides or derivatives and variants thereof, the proper folding is typically the arrangement that results in optimal biological activity, and can conveniently be monitored by assays for activity, e.g. ligand binding, enzymatic activity, etc.

In some instances, for example where the desired product is of synthetic origin, assays based on biological activity will be less meaningful. The proper folding of such molecules may be determined on the basis of physical properties, energetic considerations, modeling studies, and the like.

In vitro synthesis: as used herein refers to the cell-free synthesis of polypeptides in a reaction mix comprising biological extracts and/or defined reagents. The reaction mix will comprise at least ATP, an energy source; a template for production of the macromolecule, e.g. DNA, mRNA, etc.; amino acids, and such co-factors, enzymes and other reagents that are necessary for the synthesis, e.g. ribosomes, tRNA, polymerases, transcriptional factors, etc. Such synthetic reaction systems are well-known in the art, and have been described in the literature. The cell-free synthesis reaction may be performed as batch, continuous flow, or semi-continuous flow, as known in the art.

Redox buffer. The synthetic reaction mix in the present invention is modified by the addition of a redox buffer. Such a buffer comprises compounds with free sulfhydryl groups and/or disulfide bonds, such as one or more of glutathione, dithiothreitol, dithioerythritol, β-mercaptoethanol, thioglycolate, cysteine, etc in either their reduced or oxidized forms or in a mixture of both. The concentration of reducing and/or oxidizing agent and the ratio of the oxidized and reduced forms necessary to achieve the reducing or oxidizing power desired for the selected reaction time will vary according to the strength of the reducing or oxidizing agent, the level of $O_2$ in the system, and the length of the reaction time.

In a preferred embodiment, glutathione is used as the redox buffering agent, and is added at a concentration of at least about 1 mM and not more than about 25 mM, preferably at a concentration of about 5 to 10 mM.

The redox buffer may comprise both the oxidized and reduced forms of the sulfhydryl compound, for example in a ratio of between about 10:1 to 1:1 of oxidized:reduced forms, usually in a ratio between about 5:1 to 2:1, and may be in a ratio of 4:1.

Biological extracts. For the purposes of this invention, biological extracts are any preparation comprising the components of a protein synthesis machinery, usually a bacterial cell extract, wherein such components are capable of expressing a nucleic acid encoding a desired protein. Thus, a bacterial extract comprises components that are capable of translating messenger ribonucleic acid (mRNA) encoding a desired protein, and optionally comprises components that are capable of transcribing DNA encoding a desired protein. Such components include, for example, DNA-directed RNA polymerase (RNA polymerase), any transcription activators that are required for initiation of transcription of DNA encoding the desired protein, transfer ribonucleic acids (tRNAs), aminoacyl-tRNA synthetases, 70S ribosomes, $N^{10}$-formyltetrahydrofolate, formylmethionine-tRNAf$^{Met}$ synthetase, peptidyl transferase, initiation factors such as IF-1, IF-2 and IF-3, elongation factors such as EF-Tu, EF-Ts, and EF-G, release factors such as RF-1, RF-2, and RF-3, and the like.

In a preferred embodiment of the invention, the reaction mixture comprises extracts from bacterial cells, e.g. *E. coli* S30 extracts, as is known in the art. For convenience, the organism used as a source of extracts may be referred to as the source organism. Methods for producing active extracts are known in the art, for example they may be found in Pratt (1984), Coupled transcription-translation in prokaryotic cell-free systems, p. 179–209, in Hames, B. D. and Higgins, S. J. (ed.), Transcription and Translation: A Practical Approach, IRL Press, New York. Kudlicki et al. (1992) *Anal Biochem* 206(2):389–93 modify the S30 *E. coli* cell-free extract by collecting the ribosome fraction from the S30 by ultracentrifugation. While such extracts are a useful source of ribosomes and other factors necessary for protein synthesis, they can also contain small amounts of enzymes responsible for undesirable side-reactions that are unrelated to protein synthesis, but which modulate the oxidizing environment of the reaction, and which can act to reduce the groups on the nascent polypeptide and the redox buffer.

In some embodiments, the synthetic reactions are performed in the substantial absence of polyethylene glycol (PEG). A conventional reaction mixture contains about 2% poly(ethylene glycol) 8000. However it is found that this diminishes the yield. In the present methods, the molecules spermidine and putrescine can be used in the place of PEG. Spermine or spermidine is then present at a concentration of at least about 0.5 mM, usually at least about 1 mM, preferably about 1.5 mM, and not more than about 5 mM. Putrescine is present at a concentration of at least about 0.5 mM, preferably at least about 1 mM, preferably about 1.5 mM, and not more than about 5 mM.

Redox optimized extracts. The biological extracts for the present methods are preferably optimized to substantially eliminate enzymes and other biomolecules present in the extract that act to reduce the redox buffer. The undesirable enzymes, may be removed or otherwise inactivated in the reaction mix.

In a preferred embodiment, the endogenous molecules having free sulfhydryl groups are inactivated prior to the initiation of synthesis by treatment with a compound that chemically blocks the sulfhydryls, e.g. by alkylation or acetylation of the free sulfhydryl. The inactivating compound may then be removed from the reaction mix, e.g. by dialysis, etc. Alternatively, the inactivating compound is added at lower concentrations such that, before the protein synthesis reaction begins, the reactivity of the inactivating compound is fully depleted by the cell extract or by sulfhydryl compounds such as cysteine or reduced glutathione.

Useful inactivating agents include iodoacetamide, N-ethyl maleimide, iodoacetate, N-iodoacetyl-N -(5-sulfo-1-naphthy) ethylene diamine, etc., as known in the art; especially those compounds including iodoacetamides, maleimides, benzylic halides and bromomethylketones. The concentration of inactivation agent and length of time for the reaction will be determined by the specific compound that is chosen. The inactivation agent is added at a concentration that substantially eliminates the endogenous sulfhydryl reducing activity, while maintaining the synthetic activity of the extract. Both activities are readily determined by methods illustrated in the listed examples. Usually at least about 50% of the synthetic activity will be retained, more usually at least about 75%, and preferably at least about 90%. As an example, where the inactivation agent is iodoacetamide, it may be added at a concentration of from about 0.5 to 5 mM, and incubated from between 15 to 60 minutes.

In addition to the use of an inactivation agent to pre-treat the biological extracts, the reducing activity of the extract may be further modified by the genetic modification of the source strain to "knock-out", or genetically inactivate enzymes having this undesirable activity. Such enzymes may include thioredoxin reductase, glutathione reductase, and the like.

The coding sequence for the enzyme is "knocked-out" or otherwise inactivated in the chromosome of the source organism, by deletion of all or a part of the coding sequence; frame-shift insertion; dominant negative mutations, etc. The genomes of a number of organisms, including *E. coli*, have been completely sequenced, thereby facilitating the genetic modifications. For example, a markerless knockout strategy method is described by Arigoni et al. (1998) *Nat Biotechnol* 16(9):851–6.

A preferred method for inactivating targeted genes is described by Hoang et al. (1998) *Gene* 212:77–86. In this method, gene replacement vectors are employed that contain a tetracycline resistance gene and a gene encoding levan sucrase (sacB) as selection markers for recombination. The target gene is first cloned and mutagenized, preferably by deleting a significant portion of the gene. This gene is then inserted by ligation into a vector designed for facilitating chromosomal gene replacement. The *E. coli* cells are then transformed with those vectors. Cells that have incorporated the plasmid into the chromosome at the site of the target gene are selected, then the plasmid is forced to leave the chromosome by growing the cells on sucrose. Sucrose is toxic when the sacB gene resides in the chromosome. The properly mutated strain is selected based on its phenotype of tetracycline sensitivity and sucrose resistance. PCR analysis or DNA sequencing then confirms the desired genetic change.

The enzyme can be removed from the cell extract after cell disruption and before use. Any of the several means known in the art of protein purification may be used, including affinity purification techniques such as the use of antibodies or antibody fragments with specific affinity for the target enzymes; use of affinity tags expressed as part of the target enzymes to facilitate their removal from the cell extract; and conventional purification methods.

For example, an antibody or antibody fragment (e.g., Fab or scFv) is selected for specific affinity for the target enzyme using phage display or other well developed techniques. That antibody or antibody fragment is then immobilized on any of several purification beads or resins or membranes using any of several immobilization techniques. The immobilized antibody is contacted with the cell extract to bind to the target enzyme, and the immobilized antibody/enzyme complex then removed by filtration or gentle centrifugation.

In another example, the coding sequence of the targeted protein may be modified to include a tag, such as the Flag® extension (developed by Immunex Corp. and sold by Stratagene), or a poly-histidine tail. Many other examples have been published and are known to those skilled in the art. The tagged proteins are then removed by passage over the appropriate affinity matrix or column. The amino acid extension and binding partner are chosen so that only specific binding occurs under conditions compatible with the stability of the cell extract, and without significantly altering the chemical composition of the cell extract.

In yet another example, the target enzyme or enzymes are separated by any of several methods commonly used for protein purification, such as substrate affinity chromatography, ion exchange chromatography, hydrophobic interaction chromatography, electrophoretic separation, or other methods practiced in the art of protein purification.

Addition of folding enzymes. The reaction mixture of the present invention may be further modified by the inclusion of one or more enzymes that enhance folding and disulfide bond formation, i.e. foldases, chaperonins, etc. In one embodiment of the invention, a bacterial foldase enzyme is added to the reaction mix. A number of cysteine oxidoreductases catalyzing disulfide bond formation have been characterized in *E. coli*, for example. Enzymes or chaperonins of interest include RotA (PpiA), FkpA, Skp, SurA, PpiD, DsbA, DsbB, DsbC, DsbD, PDI (protein disulfide isomerase), GroEL/ES, DnaK, DnaJ, GrpE, BIP (immunoglobulin heavy chain binding protein), PPI (peptidylprolyl isomerase) and cyclophilins, etc. (see Schafer et al. (1999) *J Biol Chem* 274(35):24567–74; Muller et al. (2001) *Prog Nucleic Acid Res Mol Biol.* 66:107–57). The folding enzyme(s) are added at a concentration effective to improve the overall activity of the target protein of interest, which may be empirically determined by titrating the biological activity of the expressed protein product.

Of particular interest is the inclusion of DsbC, a soluble enzyme with oxidase and isomerase activity that catalyzes the rearrangement, or isomerization, of incorrect disulfide bonds. Incorrect pairing of cysteine residues occurs readily when an unfolded polypeptide chain is first oxidized. DsbC facilitates the disruption of incorrect disulfide bonds and the subsequent formation of those that occur in the native state. Also of interest is the use of the soluble enzyme DsbA, which is a main catalyst of disulfide bond formation.

Identification of the DsbC gene is described by Missiakas et al. (1994) *EMBO J.* 13:2013–2020, where it is shown to have an activity similar to that of DsbA in the dithiothreitol-dependent reduction of insulin in vitro. Also see Chen et al. (1999) *J. Biol. Chem.* 274:19601–19605. The use of DsbA or DsbC for enhancing periplasmic folding is discussed by Joly et al. (1998) *P.N.A.S.* 95:2773–2777.

Bacterial periplasmic chaperone proteins belong to two major groups, the Dsb proteins catalyzing thiol-disulfide exchange reactions, and peptidyl prolyl isomerases (PPIases) catalyzing the cis-trans isomerization around Xaa-Pro peptidyl bonds. Representatives of all major families of PPIases have been detected in the periplasm of Gram-negative bacteria, including RotA (PpiA), which is a cyclophilin-type PPIase; FkpA, a FK506-binding protein type PPIase; and SurA and PpiD, which belong to the parvulin type. In addition, Skp functions as a periplasmic chaperone. This 16-kDa, basic *E. coli* protein is a homolog of the Salmonella OmpH protein, which acts a molecular chaperone preventing premature folding of preproteins, and in the generation and maintenance of early soluble folding intermediates.

As an alternative to bacterial enzymes, eukaryotic enzymes may be used. For example, the eukaryotic PDI is not only an efficient catalyst of protein cysteine oxidation and disulfide bond isomerization, but also exhibits chaperone activity. Co-expression of PDI can even facilitate the production of active proteins having multiple disulfide bonds.

The terms "desired protein" or "selected protein" are used interchangeably and refer generally to any peptide or protein having more than about 5 amino acids. The polypeptides may be homologous to, or preferably, may be exogenous, meaning that they are heterologous, i.e., foreign, to the bacteria from which the bacterial cell-free extract is derived, such as a human protein or a yeast protein produced in the bacterial cell-free extract. Preferably, mammalian polypeptides, i.e. polypeptides encoded in a mammalian genome are used.

Examples of mammalian polypeptides include, but are not limited to, molecules such as renin; growth hormones, including human growth hormone and bovine growth hormone; growth hormone releasing factor; parathyroid hormone; thyroid stimulating hormone; lipoproteins; alpha-1-antitrypsin; insulin A-chain; insulin; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES and other chemokines; human macrophage inflammatory protein (MIP-1α); a serum albumin such as human serum albumin; mullerian-inhibiting substance; relaxin A-chain; relaxin B-chain; pro-relaxin; mouse gonadotropin-associated peptide; a microbial protein, such as betalactamase; DNase; inhibin; activin; vascular endothelial growth factor (VEGF); receptors for hormones or growth factors; integrin; protein A or D; rheumatoid factors; a neurotrophic factor such as bone-derived neurotrophic factor (BDNF), neurotrophin-3,-4, -5, or -6 (NT-3, NT-4, NT-5, or NT-6), or a nerve growth factor such as NGF-β; platelet-derived growth factor (PDGF); fibroblast growth factor such as αFGF and βFGF; epidermal growth factor (EGF); transforming growth factor (TGF) such as TGF-α and TGF-β, including TGF-β1, TGF-β2, TGF-β3, TGF-β4, or TGF-β5; insulin-like growth factor-I and -II (IGF-I and IGF-II); des(1–3)IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-α, -β, and -γ; colony stimulating factors (CSFs), e.g., M-CSF, GM-CSF, and G-CSF; interleukins (ILs), e.g., IL-1 to IL-18; superoxide dismutase; T-cell receptors; surface membrane proteins; decay accelerating factor; viral antigen such as, for example, a portion of the AIDS envelope; transport proteins; homing receptors; addressins; regulatory proteins; antibodies; and fragments of any of the above-listed polypeptides.

Methods for Enhanced In Vitro Synthesis

The subject system is useful for in vitro protein synthesis of biologically active proteins, particularly proteins requiring correct formation of one or more disulfide bonds for biological activity. The synthesis reactions may include the transcription of RNA from DNA or RNA templates. The reactions may utilize a large scale reactor, small scale, or may be multiplexed to perform a plurality of simultaneous syntheses. Continuous reactions will use a feed mechanism to introduce a flow of reagents, and may isolate the end-product as part of the process. Batch systems are also of interest, where additional reagents may be introduced to prolong the period of time for active synthesis. A reactor may be run in any mode such as batch, extended batch, semi-batch, semi-continuous, fed-batch and continuous, and which will be selected in accordance with the application purpose.

Of particular interest is the translation of mRNA to produce proteins, which translation may be coupled to in vitro synthesis of mRNA from a DNA template. Such a cell-free system will contain all factors required for the translation of mRNA, for example ribosomes, amino acids, tRNAs, aminoacyl synthetases, elongation factors and initiation factors. Cell-free systems known in the art include wheat germ extracts (Roberts et al. (1973) P.N.A.S. 70:2330), reticulocyte extracts (Pelham et al. (1976) Eur. J. Biochem. 67:247), E. coli extracts, etc., which can be treated with a suitable nuclease to eliminate active endogenous mRNA.

In addition to the above components such as cell-free extract, genetic template, amino acids and energy sources, materials specifically required for protein synthesis may be added to the reaction. These materials include salt, polymeric compounds, cyclic AMP, inhibitors for protein or nucleic acid degrading enzymes, inhibitor or regulator of protein synthesis, oxidation/reduction adjuster, non-denaturing surfactant, buffer component, spermine, spermidine, etc.

The salts preferably include potassium, magnesium, ammonium and manganese salt of acetic acid or sulfuric acid, and some of these may have amino acids as a counter anion. The polymeric compounds may be polyethylene glycol, dextran, diethyl aminoethyl, quaternary aminoethyl and aminoethyl. The oxidation/reduction adjuster may be dithiothreitol, ascorbic acid, glutathione and/or their oxides. Also, a non-denaturing surfactant such as Triton X-100 may be used at a concentration of 0–0.5 M. Spermine and spermidine may be used for improving protein synthetic ability, and cAMP may be used as a gene expression regulator.

When changing the concentration of a particular component of the reaction medium, that of another component may be changed accordingly. For example, the concentrations of several components such as nucleotides and energy source compounds may be simultaneously controlled in accordance with the change in those of other components. Also, the concentration levels of components in the reactor may be varied over time.

Preferably, the reaction is maintained in the range of pH 5–10 and a temperature of 20°–50° C., and more preferably, in the range of pH 6–9 and a temperature of 25°–40° C. To optimize protein folding, the temperature may be varied, e.g. by reducing the temperature to about 25°, about 30°, about 32°, about 35°, about 37°, and the like.

When using a protein isolating means in a continuous operation mode, the product output from the reactor flows through a membrane into the protein isolating means. In a semi-continuous operation mode, the outside or outer surface of the membrane is put into contact with predetermined solutions that are cyclically changed in a predetermined order. These solutions contain substrates such as amino acids and nucleotides. At this time, the reactor is operated in dialysis, diafiltration batch or fed-batch mode. A feed solution may be supplied to the reactor through the same membrane or a separate injection unit. Synthesized protein is accumulated in the reactor, and then is isolated and purified according to the usual method for protein purification after completion of the system operation.

Where there is a flow of reagents, the direction of liquid flow can be perpendicular and/or tangential to a membrane. Tangential flow is effective for recycling ATP and for preventing membrane plugging and may be superimposed on perpendicular flow. Flow perpendicular to the membrane may be caused or effected by a positive pressure pump or a vacuum suction pump. The solution in contact with the outside surface of the membrane may be cyclically changed, and may be in a steady tangential flow with respect to the membrane. The reactor may be stirred internally or externally by proper agitation means.

During protein synthesis in the reactor, the protein isolating means for selectively isolating the desired protein may include a unit packed with particles coated with antibody molecules or other molecules immobilized with a component for adsorbing the synthesized, desired protein, and a membrane with pores of proper sizes. Preferably, the protein isolating means comprises two columns for alternating use. Alternately, the protein product may be absorbed using expanded bed chromatography, in which case a membrane may or may not be used.

In embodiments using DNA template to drive in vitro transcription/translation, some components of the transcription and/or translation system in the bacterial extract can be advantageously supplemented to increase the availability of such components in the reaction mixture. In a preferred embodiment, the reaction mixture contains one or more of the following: (1) an initial concentration of GTP, UTP and CTP of about 0.5 mM to about 2.0 mM, and preferably about 0.85 mM; (2) an initial concentration of ATP of about 0.5 mM to about 2.5 mM, and preferably about 1.22 mM; (3) an initial concentration of PEP of about 10 mM to about 50 mM, and preferably about 27.0 mM; (4) a concentration of pyruvate kinase of about 0.05 units/ml to about 0.5 units/mL, and preferably about 0.2 units/mL; (5) an initial concentration of tRNAs of about 0.05 mg/mL to about 0.3 mg/mL, and preferably about 0.17 mg/mL; (6) an initial concentration of all 19 amino acids (all amino acids except methionine) of about 0.2 mM to about 0.6 mM, and preferably about 0.35 mM; and (7) an initial concentration of methionine of about 0.6 micromoles/liter ($\mu$M) to about 2.0 mM, and preferably about 4.3 $\mu$M to about 2.0 mM, and more preferably about 0.1 mM to about 2.0 mM, and most preferably about 1.0 mM to about 2.0 mM.

Optimizations of Conditions

In one embodiment of the invention, methods are provided for screening in vitro synthesis reaction conditions in order to optimize folding and correct formation of disulfide bonds. A plurality of reactions having a stable redox potential are assayed for synthesis of the active form of a protein containing at least one disulfide bond, i.e. a protein that is correctly folded.

The reaction conditions are optimized by varying the level of compounds that irreversibly inactivate free sulfhydryl groups, and by introducing selected chaperone and foldase protein(s); varying temperature; varying the concentration of the redox buffer as well as the ratio of oxidized to reduced forms; and the like.

A typical assay contains a control sample, which may be a conventional reaction mixture, and/or a redox stabilized reaction mixture. The reaction conditions may be optimized by adding or varying the concentrations of one or more of RotA (PpiA), FkpA, Skp, SurA, PpiD, DsbA, DsbB, DsbC, DsbD, PDI, GroEL/ES, DnaK, DnaJ, GrpE, BIP, PPI, PDI, cyclophilin, etc. to at least one and usually a plurality of reactions to form a panel of reaction conditions. The change in synthesis of active protein in response to the agent is measured. Reaction conditions may also be optimized by varying the temperature, varying the concentration of inactivating agent, and varying the ratio of oxidized to reduced forms of the redox buffer to form a plurality of reaction conditions, which may be displayed as a matrix of possible combinations.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in synthesis.

The amount of protein produced in a translation reaction can be measured in various fashions. One method relies on the availability of an assay, which measures the activity of the particular protein being translated. An example of an assay for measuring protein activity is a luciferase assay system, or chloramphenical acetyl transferase assay system. These assays measure the amount of functionally active protein produced from the translation reaction. Activity assays will not measure full length protein that is inactive due to improper protein folding or lack of other post translational modifications necessary for protein activity.

Another method of measuring the amount of protein produced in coupled in vitro transcription and translation reactions is to perform the reactions using a known quantity of radiolabeled amino acid such as $^{35}$S-methionine or $^{3}$H-leucine and subsequently measuring the amount of radiolabeled amino acid incorporated into the newly translated protein. Incorporation assays will measure the amount of radiolabeled amino acids in all proteins produced in an in vitro translation reaction including truncated protein products. The radiolabeled protein may be further separated on a protein gel, and by autoradiography confirmed that the product is the proper size and that secondary protein products have not been produced.

It is to be understood that this invention is not limited to the particular methodology, protocols, cell lines, animal species or genera, constructs, and reagents described, as such may, of course, vary. It is also to be understood that the terminology used herein is for the purpose of describing particular embodiments only, and is not intended to limit the scope of the present invention which will be limited only by the appended claims.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the cell lines, constructs, and methodologies that are described in the publications, which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Experimental

EXAMPLE 1

Expression of the serine Protease Domain of Murine Urokinase in a Cell-Free System The standard reaction mixture for cell-free protein synthesis consists of the following components: 57 mM Hepes-KOH (pH 8.2), 1.2 mM ATP, 0.85 mM each of GTP, UTP and CTP, 0.64 mM cAMP, 200 mM potassium glutamate, 80 mM NH$_4$(OAc), 15 mM Mg(OAc)$_2$, 34 µg/ml folinic acid, 6.7 µg/ml plasmid, 33 µg/ml T7RNA polymerase, 500 µM each of 20 unlabeled amino acids and [$^{3}$H] leucine (0.27 GBq/mmol), 2% PEG 8000, 33 mM PEP(phosphoenolpyruvate), 1 mM reduced glutathione(GSH), 4 mM oxidized glutathione (GSSG) and 0.24 volumes of S30 extract. For the expression of serine protease domain of murine urokinase, plasmid pK7UK which contains the coding sequence under the T7 promoter was used.

In certain experiments, E. coli dsbC or human PDI protein was added in different concentrations. PDI was purchased from Pierce, Inc. and dsbC was purified from the culture of E. coli strain BL21DE3 (pETdsbChisC). T7 RNA polymerase was prepared from the culture of E. coli strain BL21(pAR1219) according to the slightly modified procedures of Davanloo et al. (1984) P.N.A.S. 81:2035–2039. E. coli strain FA113 which carries mutations in the trxB and gor genes was also used.

S30 extract was prepared from E. coli K12 (strain A19) according to the procedures reported in Pratt (1984) Coupled Transcription-Translation in Prokaryotic Cell-free Systems, p. 179–209. In Hames, B. D. and Higgins, S. J. (ed.), Transcription and Translation: a Practical Approach. IRL Press, New York. For further treatment of S30 extract, the extract was mixed with 0.1 volume of 20 mM iodoacetamide (IAM) and incubated for 30 minutes at room temperature. To remove the residual IAM or sodium sulfite, the extract was dialyzed against 200 volumes of S30 buffer(10 mM Tris-Cl, pH 7.8, 14 mM Mg(OAc)$_2$, 60 mM K(OAc)) at 4° C. for 4 hours.

For the expression of protein in the semicontinuous system, 210 µl of standard reaction mixture was incubated in a dialysis chamber (Slide-A-Lyzer, molecular weight cut-off 10,000, Pierce, IL) which was placed in 6.0 mL of reservoir buffer (same as the reaction mixture except for the absence of S30 extract, DNA, and T7 RNA polymerase).

All the synthesis reactions were conducted at 37° C. for the given time periods.

Determination of Protein Synthesis Yield. The amount of synthesized protein was estimated from the measured TCA-insoluble radioactivities in a liquid scintillation counter (LS3801, Beckman) as described by Kim, et al. (1996) Eur. J. Biochem. 239: 881–886.

Enzymatic Activity of Cell-Free Synthesized Protease Domain of Urokinase. 20 μL samples were taken during incubation periods to measure the enzymatic activity of synthesized protein. After centrifuging the samples, 10 μL of supernatant was taken and added to a microplate containing 80 μL of assay buffer (38 mM NaCl, 50 mM Tris-Cl, pH 8.8) and 10 μL of substrate solution (2 mM Chromozyme U, Roche Molecular Biochemicals, CA). The change in absorbance at 405 nm was measured in a microplate reader (SpectraMax 190, Molecular Devices, CA).

Analysis of Reduced Glutathione Concentration. The concentration of reduced glutathione was measured using dithionitrobenzoic acid (DTNB). A 4.0 mg/mL DTNB solution was prepared in 1M Tris-Cl solution (pH 7.8). 10 μL samples were mixed with the same volume of 10% TCA to stop the enzymatic reduction and centrifuged. To determine the concentration of reduced glutathione, 10 μL of supernatant and 10 μL of DTNB solution were added to 80 μL of 1M Tris-Cl solution in a microplate. After 3 minutes, absorbances at 412 nm were measured and the concentration of glutathione was determined from a standard curve. Although other reduced sulfhydryl compounds may be present in the sample and may contribute to the final measured value, the concentration of reduced glutathione generally dominated.

Construction of mutant strains. Insertional mutations in trxB or gor in the strain FA113 (Bessette et al. (1999) P.N.A.S. 96(24):13703–8) were moved into strain A19 by P1 transduction following the standard procedures (Miller (1992) A Short Course in Bacterial Genetics. p. 263–364. Cold Spring Harbor Press, N.Y.)

Results

Figure 1:
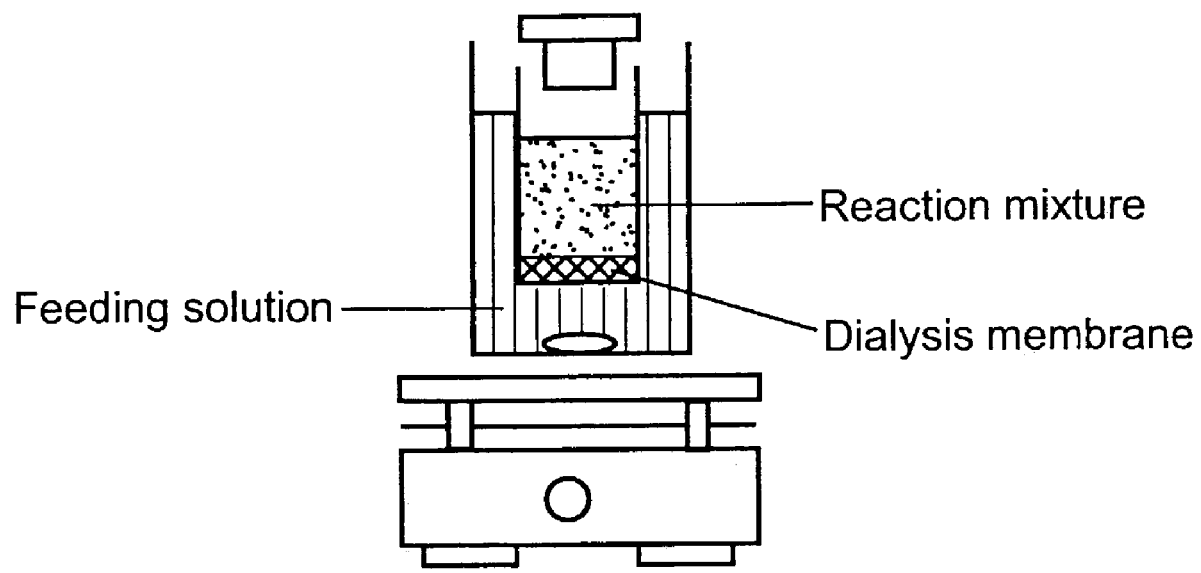
FIG. 1 shows the reactor used for the semicontiunous reactions.
Figure 2:
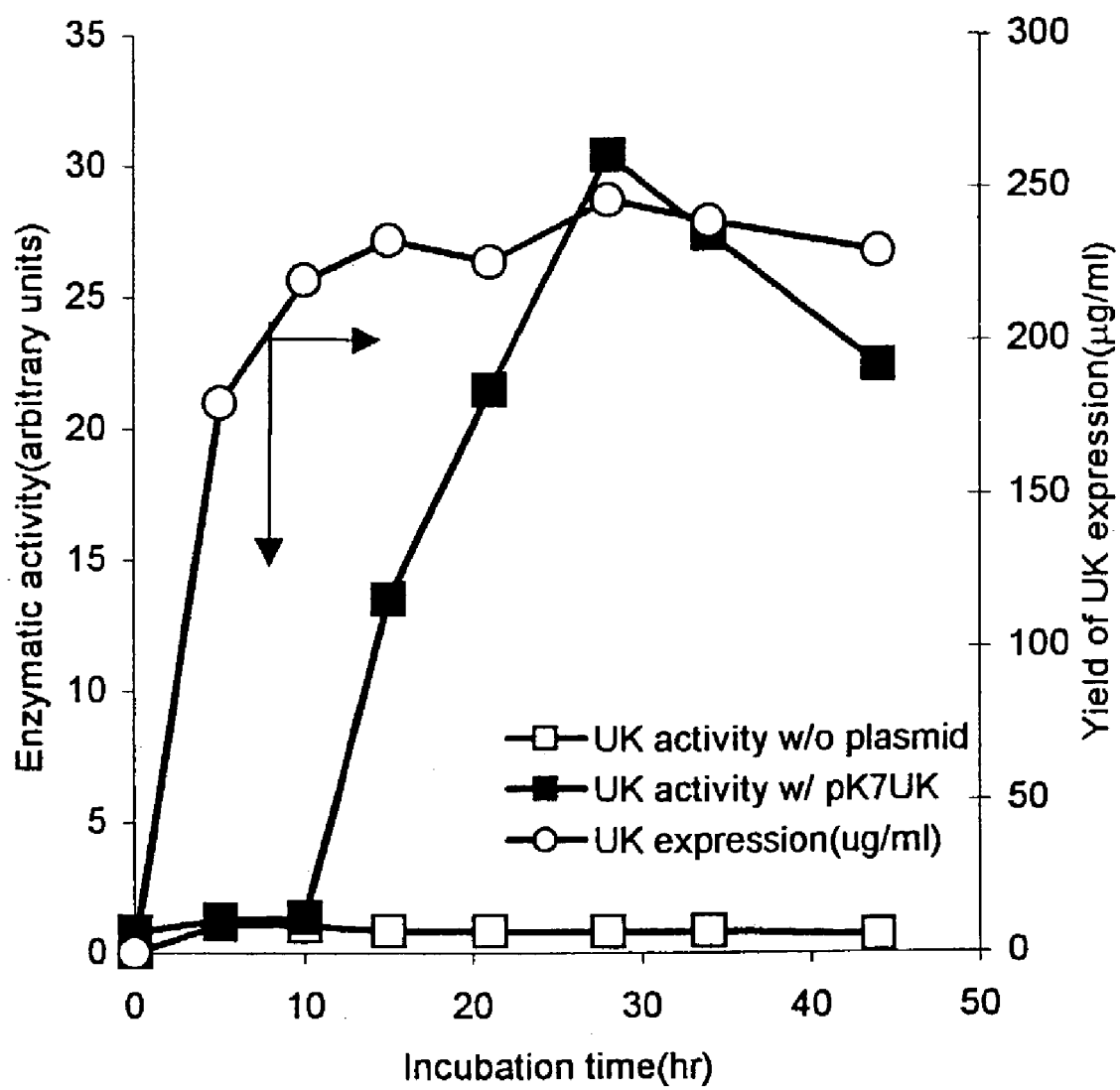
FIG. 2 is a graph depicting the synthesis of urokinase and its enzymatic activity during a semi-continuous reaction.

210 μL of reaction mixture was prepared and incubated in the semi-continuous reactor depicted in FIG. 1. 10 μL samples were withdrawn during the incubation to determine the amount of synthesized protein (shown in FIG. 2, open circles). At the same time, 20 μL samples were taken for the measurement of serine protease activity (open squares, reaction without plasmid; filled squares, reaction with the plasmid pK7UK).

Figure 3:
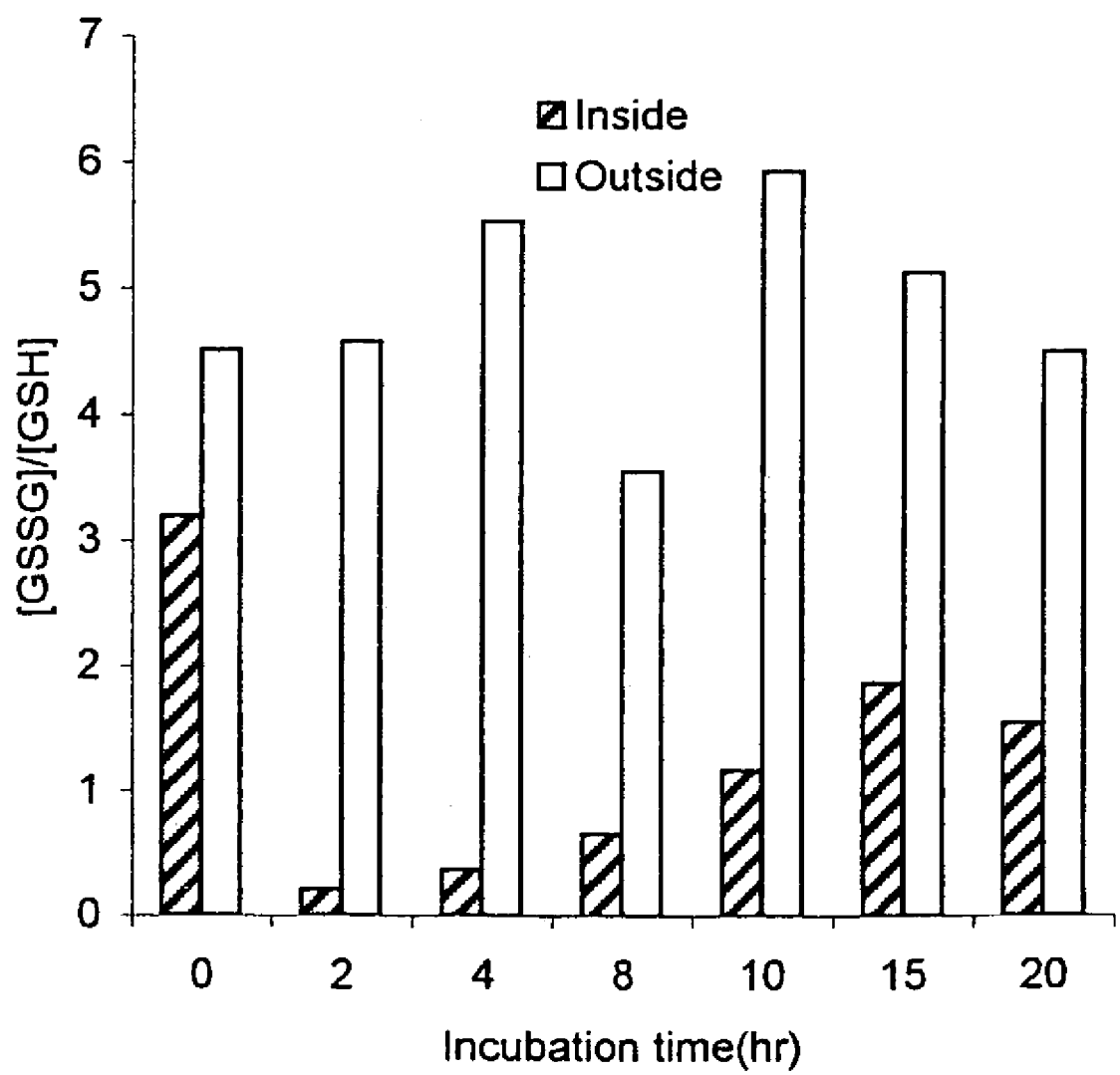
FIG. 3 is a bar graph depicting the change in redox potential during semi-continuous synthesis.

To monitor the change in redox potential, 10 μL samples were taken from the reaction mixture and reservoir solution. The concentrations of reduced glutathione were measured as described in materials and methods. Concentrations of oxidized glutathione were estimated based on the initial concentrations and the measured amounts of reduced glutathione. The results are shown in FIG. 3. The initial concentrations of reduced and oxidized glutathione were 1 mM and 4 mM, respectively.

Figure 4:
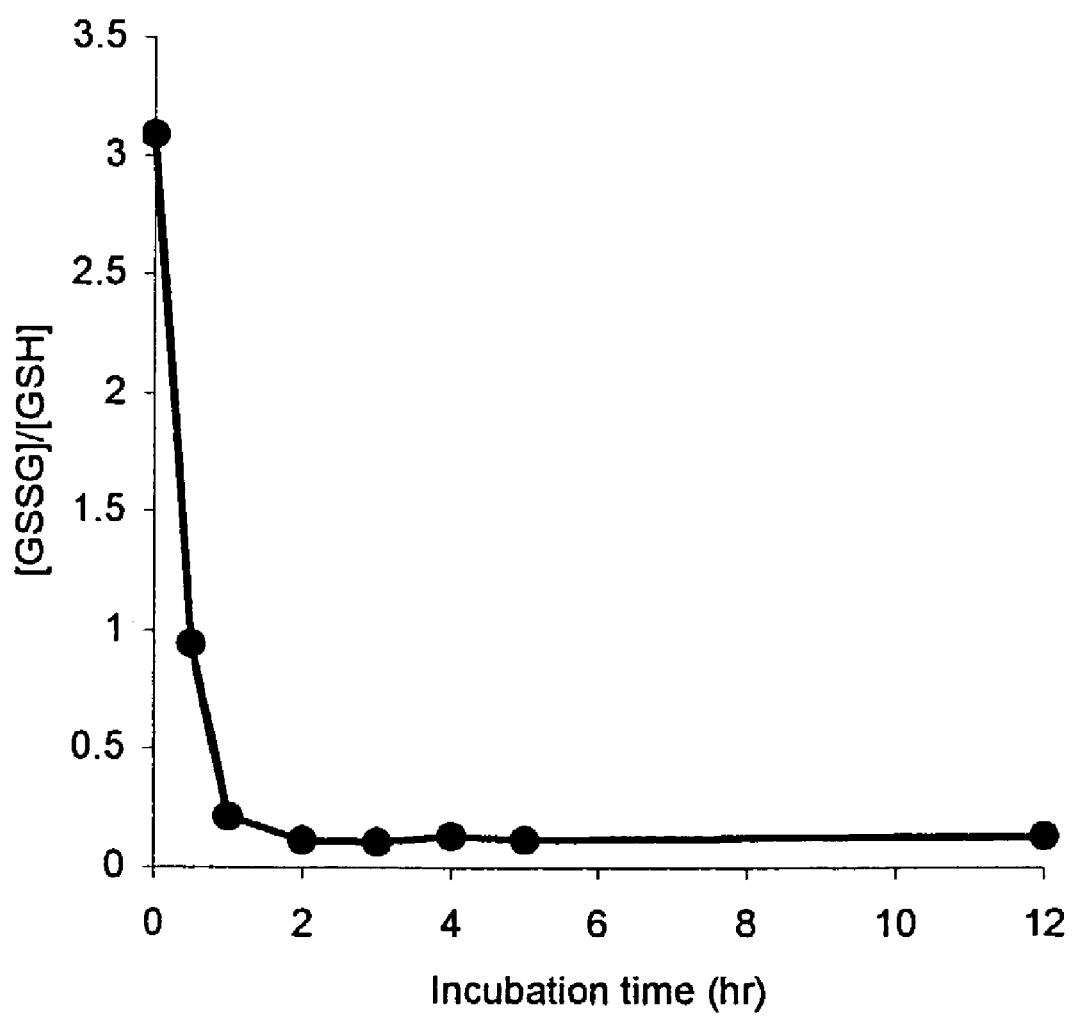
FIG. 4 is a time course showing the reduction of glutathione in a batch synthesis reaction.

To monitor the time course of reduced glutathione in a batch reaction, during the incubation of a 150 μL batch reaction, 10 μL samples were taken at the given time points, treated with TCA solution, and the concentrations determined. The concentrations of reduced glutathione were measured as described in materials and methods. Concentrations of oxidized glutathione were estimated based on the initial concentrations and the measured amounts of reduced glutathione. The results are shown in FIG. 4. The initial concentrations of reduced and oxidized glutathione were 1 mM and 4 mM respectively.

Figure 5:
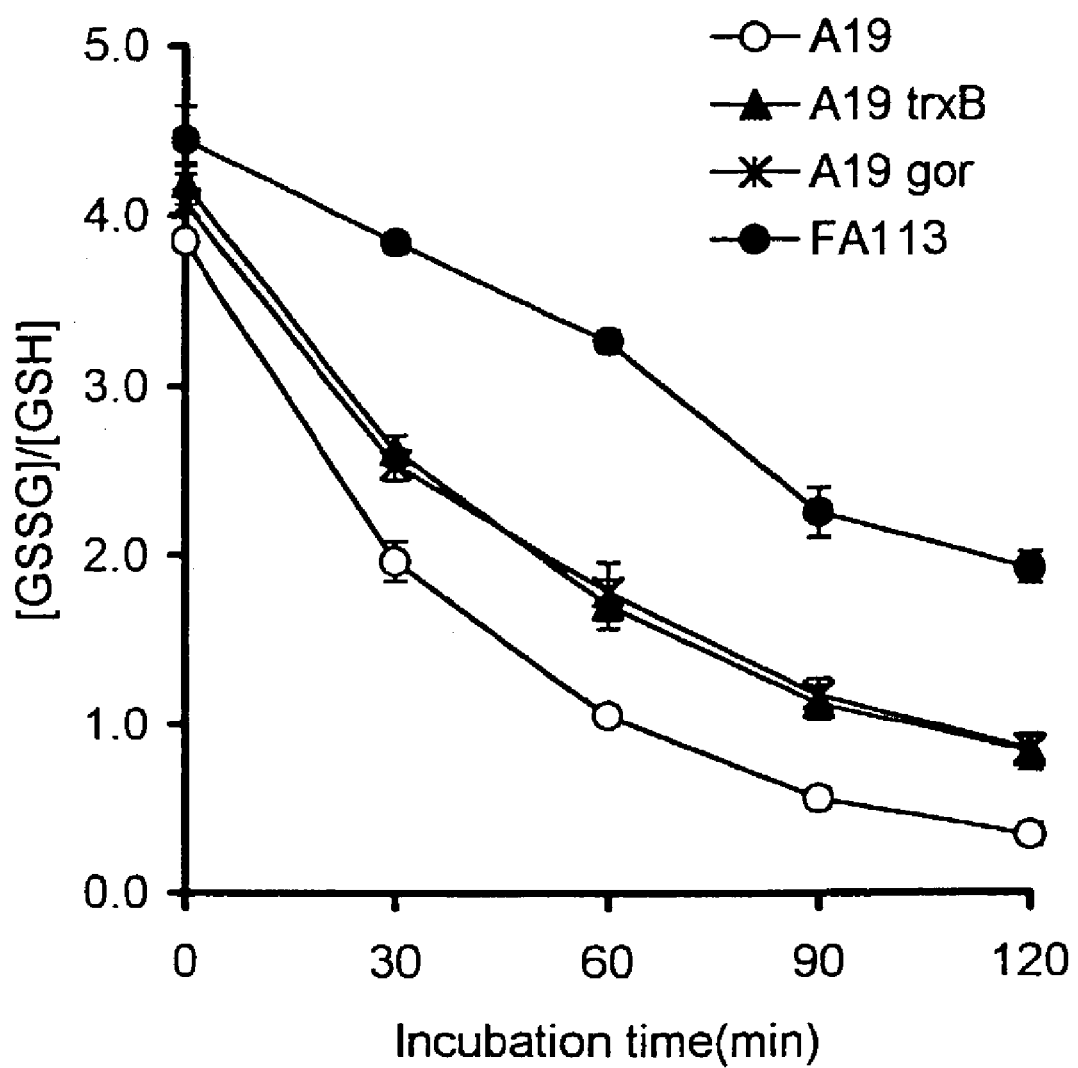
FIG. 5 shows the reduction of glutathione in the presence of extracts from different bacterial strains.

To determine the effects of different strains on glutathione reduction, cell extracts were prepared from the mutant strains indicated in FIG. 5, and were incubated with the reaction mix. 10 μL samples were taken at the given time points, treated with TCA solution and the concentrations of GSH determined as described above. Cell extracts were prepared by brief sonication of cell paste resuspended in S30 buffer. Total concentrations of cellular proteins in the reaction mixtures were 6.8 (A19); 5.2 (A19 trxB); 5.5 (A19 gor); and 5.4 (FA113) mg/mL, respectively. In experiments with the A19 cell extract used for protein synthesis the concentration of cellular protein was 10.8 mg/mL.

Figure 6:
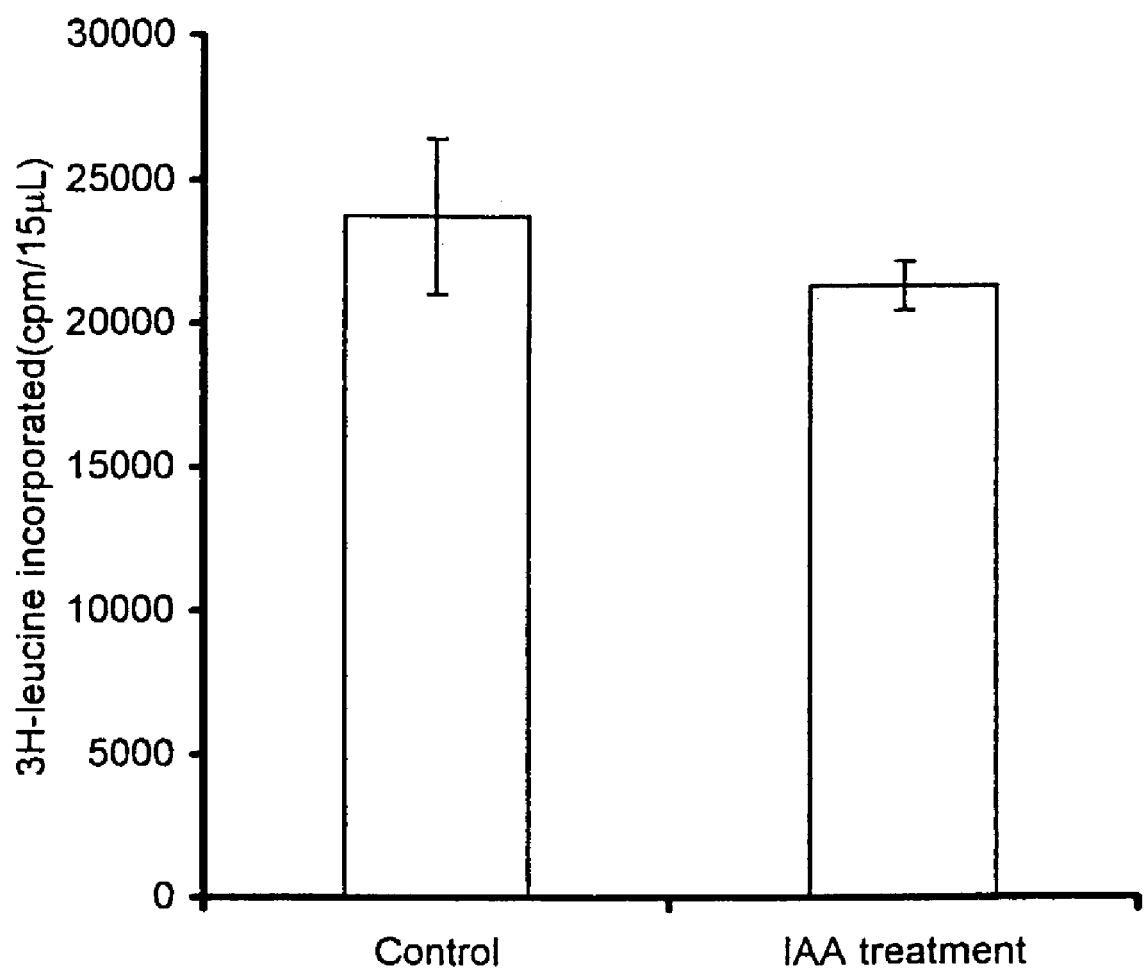
FIG. 6 is a bar graph depicting the expression of urokinase in control and IAM treated extracts.

The expression of urokinase was determined from the IAM-treated extract, as shown in FIG. 6. Plasmid pK7UK was treated in the standard reaction mixtures containing normal or IAM treated cell extract. After a 1 hour incubation, amounts of TCA-insoluble radioactivities were measured as described in the experimental methods.

Time courses of glutathione reduction and enzymatic activity of the expressed protein in a batch reaction are shown in FIG. 7. Plasmid pK7UK was expressed in a 450 μL reaction mixture containing either untreated or IAM treated S30 extract and 5 mM glutathione buffer (1 mM reduced form and 4 mM oxidized form). At the given time points, 401 μL samples were withdrawn and assayed for GSH concentration(panel A) and enzymatic activity(panel B) as described in the Materials and Methods. Open circles, reaction with normal cell-extract; closed circles, reaction with IAM treated cell-extract.

Figure 8:
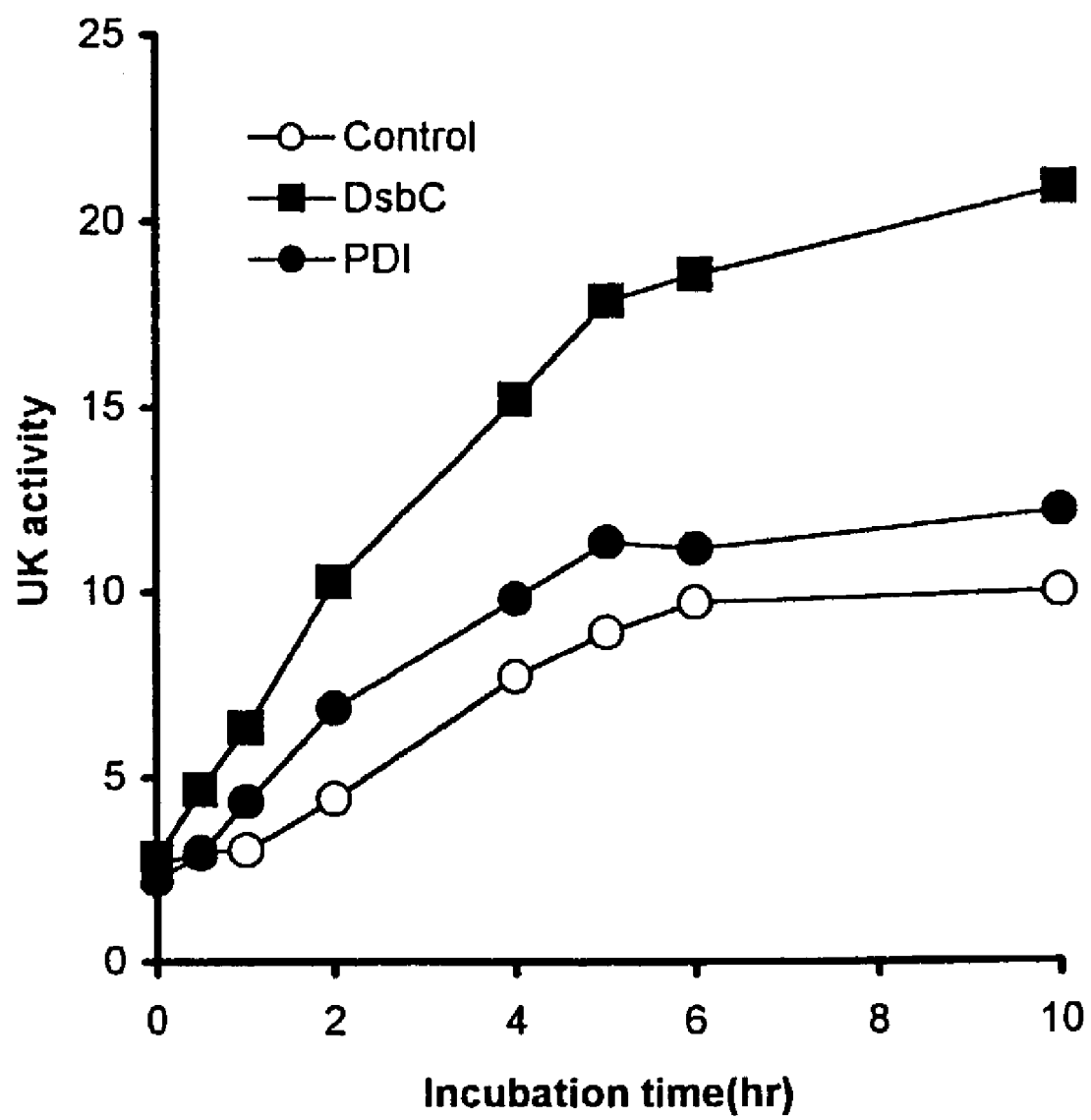
FIG. 8 is a time course of the synthesis of urokinase in the presence of PDI or dsbC.

In FIG. 8, the effect of PDI or dsbC on the rate of active protein syntheis is shown. To a reaction with IAM treated cell extract, 133 μg/mL dsbC or 27 μg/mL of PDI was added. 20 μL samples were taken during the incubation and the enzymatic activities were measured as described. Open circles (control reaction without foldase); closed circles (addition of PDI); closed squares (addition of DsbC).

EXAMPLE 2

Plasminogen activators (PAs) are serine proteases that convert the inactive proenzyme plasminogen to its active form, plasmin, which then efficiently solubilizes the fibrin mesh that forms the core of a blood clot. Plasminogen activators have important clinical significance as thrombolytic agents for the management of stroke and myocardial infarction. Wild-type t-PA is a 527-amino acid serine protease with 35 cysteine residues. It contains 17 disulfide bonds and is comprised of five distinct structural domains. vtPA is the variant of human tissue-type plasminogen activator that lacks the finger, epidermal growth factor and kringle 1 domains and has 9 disulfide bonds. Remarkable achievement has been made in the expression of active tPA in vivo. However, PA made in recombinant CHO cells and in E. coli both required complicated purification processes. In addition, the production of PA in E. coli normally requires in vitro refolding. Yields of in vitro production of PA are still relatively low.

In this work, the study of cell-free expression of active vtPA protein was carried out. To maintain a stable redox potential, free sulfhydryls in the cell extract were alkylated with iodoacetamide (IAM). In the presence of oxidized GSSG, DsbC and the chaperone, Skp, protein folding was significantly enhanced in the modified cell-free system. The effect of the physical chemical environment on protein synthesis and folding was also investigated.

Materials and Methods

The standard cell-free reaction mixture used herein includes 16 mM magnesium acetate, 80 mM ammonium acetate, 230 mM potassium glutamate, 57.2 mM HEPES-KOH buffer (pH 7.5), 1.2 mM ATP, 0.86 mM GTP, 0.86 mM UTP, 0.86 mM CTP, 34 μg/mL folinic acid, 170.6 μg/mL *E. coli* tRNA, 20 amino acids (2 mM for each), 0.03 M phosphoenolpyruvate (PEP), 0.33 mM NAD, 0.27 mM CoenzymeA, 2.69 mM oxalic acid, 2% (w/v) PEG 8000, 4.2 μM $^{14}$C-Leucine, 0.07 mg/mL T7 RNA polymerase, and 24% (v/v) S30 extract. 6.8 μg/mL of plasmid of pK7vtPA that includes the vtPA sequence between the T7 promoter and T7 terminator was used as the template for vtPA synthesis. This system was used to express vtPA in vitro. The 15 μL reaction mixture was incubated at 37° C. for 3 hours. To enhance multidisulfide protein folding in the cell-free system, this standard system was modified as described.

To eliminate disulfide reducing activity, the cell extract was mixed with iodoacetamide (concentration as indicated) and incubated at room temperature for 30 minutes prior to being added to the cell-free reaction mixture. 5 mM oxidized plus reduced glutathione with different ratios, 75 μg/mL DsbC, 1.5 mM spermidine, 1.0 mM putrescine and 300 μg/mL Skp were added to reaction mixtures before template DNA addition to enhance disulfide bond formation and protein folding. The PEG 8000 was omitted.

PEP and *E. coli* tRNA mixture were purchased from Roche Molecular Biochemicals (Indianapolis, Ind.). $^{14}$C-Leucine was from Amersham Pharmacia Biotechnology (Uppsala, Sweden). Magnesium acetate, ammonium acetate, HEPES and KOH were from Mallinckrodt (Paris, Ky.). All the other reagents were from Sigma (St. Louis, Mo.) without further purification.

S30 cell extract was prepared from *E. coli* K12 (strain A19) according to the procedures of Pratt (Pratt, 1984). To get a relatively oxidized environment, no $_{DL}$-dithiothreitol was added to the cell lysate after homogenization. T7 RNA polymerase was prepared from the culture of *E. coli* strain BL21(pAR1219) according to the procedures of Davanloo et al (Davanloo et al, 1984). *E. coli* DsbC was prepared by over expressing strain BL21(DE3) (pETDdsbChisC) and purified with cobalt IMAC column. *E. coli* Skp was purified from the culture of BL21(DE3)plys (pK7Skp) according to the slightly modified protocol of Cock et al (1999). The recovery of Skp was enhanced by using the washing buffer with lower ionic strength for the CM Sepharose column.

Measurement of protein synthesis yield. The amount of synthesized protein was estimated from the measured TCA-precipitated radioactivities in a liquid scintillation counter (LS3801, Beckman Coulter, Inc.). After centrifuging samples at 4° C., 15000 RCF, for 15 minutes, supernatants were taken and used to determine soluble yield by TCA precipitation and scintillation counting.

Reduced sulfhydral concentration assay. 10 μL samples were mixed with the same volume of 10% TCA to stop the enzymatic reaction and precipitate macromolecules. The mixture was incubated on ice for 15 minutes. After centrifugation (15000 RCF for 15 minutes), 10 μL of supernatant and the same volume of DTNB solution (4 mg/mL, prepared in 1 M Tris-Cl buffer, pH 7.8) were added to the well of 96-well plate containing 80 μL Tris-Cl buffer. Absorbances at 412 nm were measured by a microplate reader (SpectralMax 190, Molecular Devices, CA) after 3 min incubation at room temperature. The concentration of free sulfhydral was calculated by comparison with reduced glutathione standards.

Enzymatic activity of cell-free synthesized vtPA. After centrifuging samples at 4° C. and 15000 RCF for 15 minutes, 10 μL of supernatant was taken and added to a well in a microplate. Afterwards, 100 μL of assay regent mixture buffer (9 parts Tris buffer and 1 part Chromozym t-PA solution; Tris buffer: 100 mM pH 8.5 Tris-Cl buffer and 0.15% (w/v) Tween 80; Chromazym t-PA solution: 4 mM Chromazym t-PA in redist. water, Roche Molecular Biochemicals, Indianapolis, Ind.) were added and mixed with the sample. The mixture was incubated at 37° C. for 10 minutes. The rate of change in absorbance at 405 nm was recorded in a microplate reader (SpectralMax 190, Molecular Devices, CA) by kinetics assay. The concentration of active vtPA was calculated by comparison with a vtPA standard.

Results

Sulfhydral redox potential control. The expression of vtPA in the standard system was conducted at 37° C. for 3 hours. Typical total and soluble yields of vtPA in the standard cell-free system were 200 μg/mL and 30 μg/mL (in 15 μL scale reactions) respectively. This soluble yield is very low and almost no PA activity was detected. We postulated that disulfide bond formation and isomerization was limiting PA folding.

Disulfide bond formation requires a relatively oxidized environment. To provide such an oxidized environment, 4 mM oxidized glutathione was added to the reaction, along with 1 mM of reduced glutathione. However after 3 hours of reaction, we found that the free -SH concentration rose from 2.3 mM to 6.5 mM. Apparently oxidized glutathione was continuously being reduced during the 3 hour cell-free reaction.

In an unstable and relatively reduced environment, disulfide bond formation is not efficient. Reducing enzymes in the cell extract reduce the GSSG during the cell-free reaction. These enzymes require sulfhydral group in the active sites. To eliminate the reducing activity, the cell extract was treated with iodoacetamide to alkylate free sulfhydryls and to inactivate the reductase.

Figure 9:
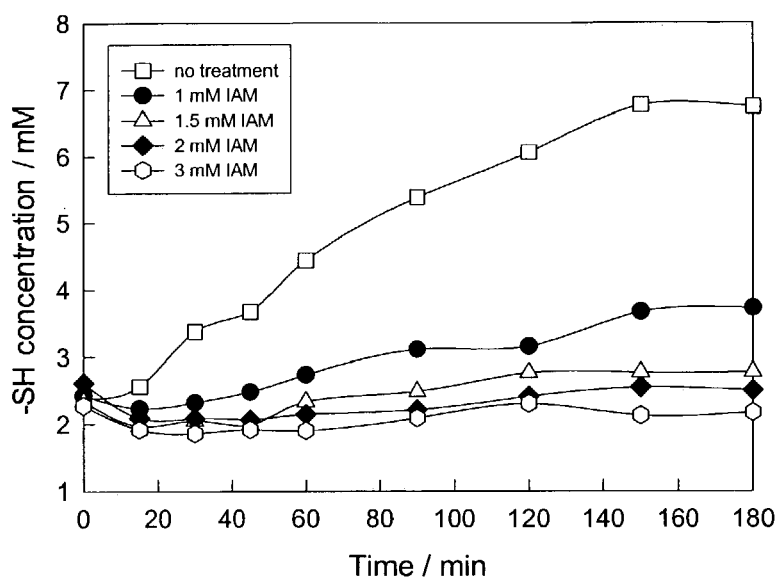
FIG. 9 is a time course of sulfhydryl concentration in a cell-free reaction. vtPA was expressed in a standard cell-free system in the presence of 4 mM GSSG and 1 mM GSH. The cell extract was pretreated with 1, 1.5, 2 and 3 mM iodoacetamide (IAM) respectively. The cell-free reaction with the cell extract omitted IAM pretreatment was run as a control. The concentration of sulfhydryls was measured at different time points.

Cell extracts were pretreated with different concentrations of iodoacetamide and the -SH concentration was monitored during a cell-free reaction. After iodoacetamide pretreatment, cell extracts were stabilized in their redox potentials (FIG. 9). As shown by our previous work, the iodoacetamide treatment has a significant effect in slowing the formation of free sulfhydryls during cell-free synthesis. With the stabilized cell-free platform, we can obtain different redox potentials by simply adding different concentrations and ratios of GSSG and GSH.

Figure 10:
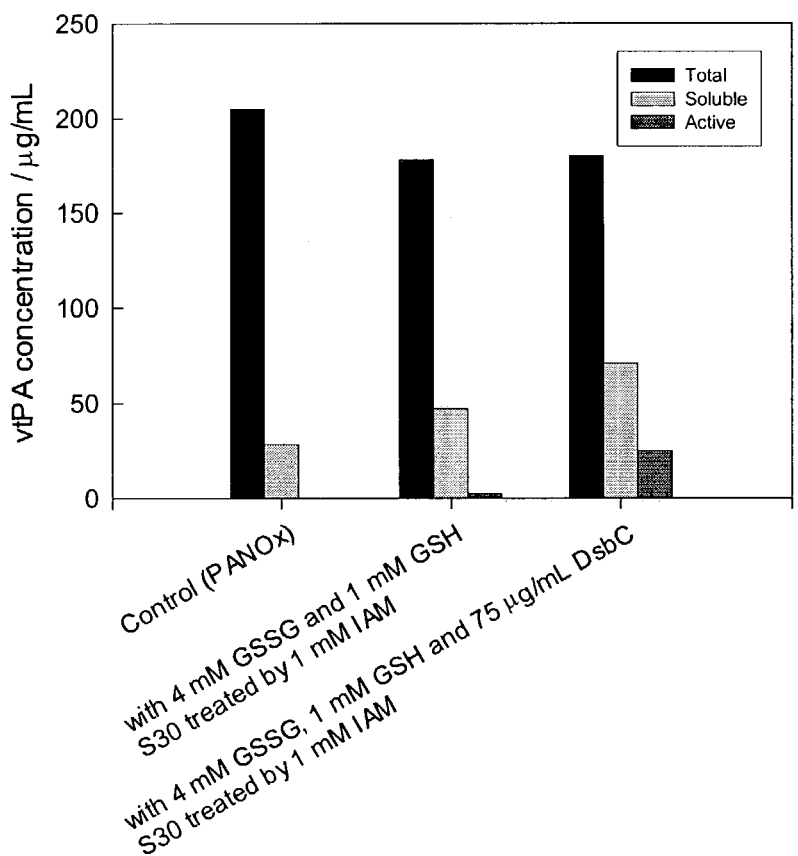
FIG. 10 shows the effect of DsbC on active vtPA expression in the cell-free system. vtPA was expressed in the standard cell-free system (control, PANOx), in the presence of 4 mM GSSG and 1 mM GSH and with 1 mM IAM cell extract pretreatment, and with 75 µg/mL DsbC addition together with 4 mM GSSG, 1 mM GSH and 1 mM IAM cell extract pretreatment. Total, soluble and active yields of vtPA were determined after 3 hours of reaction.

By using iodoacetamide treated cell extract to catalyze the cell-free reaction, we found that soluble yield was improved distinctly and reached 50 μg/mL in the presence of 4 mM GSSG and 1 mM GSH. However, as shown by FIG. 10, the active yield didn't increase significantly with the increase in soluble yield, even under the conditions of stable and relatively oxidized redox potential.

There are several catalysts and chaperones in cell extracts which potentially can promote disulfide bond formation and protein folding. The treatment of the cell extract with iodoacetamide may reduce helper proteins activity. For example, DsbC, a periplasmic disulfide bond isomerase, is known to require free sulfhydryls for activity. Since iodoacetamide treatment may inactivate the endogenous DsbC, reduced DsbC was added to accelerate disulfide isomerization in the cell-free system. Results shown in FIG. 10 indicate that 75 μg/mL DsbC improves vtPA solubility and activity. In the presence of DsbC, the concentration of iodoacetamide used in the cell extract pretreatment was optimized for maximal vtPA activity. FIG. 11 suggests that a 1 mM iodoacetamide pretreatment produces the best active vtPA yields in the presence of 4 mM GSSG, 1 mM GSH and 75 μg/mL DsbC. In contrast, the highest soluble yield was reached when the pretreatment was omitted but GSSG/GSH and DsbC were still added. However, in this case, only a tiny part of soluble protein was active (as little as 5 µg/mL). Thus the solubility of expressed protein doesn't reflect its biological activity and solubility should not be used as a surrogate objective function. For vtPA, a stable and relatively oxidized redox environment and an active disulfide bond isomerase are required to produce properly folded protein in our cell-free protein synthesis system.

To further improve vtPA production, different redox potentials were tested by adjusting the ratio of GSSG and GSH (the total concentration of GSSG plus GSH was kept constant at 5 mM.). The cell extract was pretreated with 1 mM IAM and 75 µg/mL DsbC was present in the reaction. The results of FIG. 12 show that the highest active yield, 26 µg/mL, of active vtPA was obtained with the ratio of 4 GSSG and 1 GSH. The decreased yield with only 5 mM GSSG and no GSH suggest some GSH may be beneficial for enhancing sulfhydryl disulfide exchange during protein folding.

More natural environment. In the standard system and modified system with redox potential control, 2% PEG is used. It has been suggested that PEG stabilizes mRNA and may help to crowd the macromolecular environment in cell-free systems. However, no PEG is found in natural systems. The function of PEG was evaluated in the modified cell-free system in the presence of 4 mM GSSG, 1 mM GSH, 75 µg/mL DsbC and with 1 mM IAM cell extract pretreatment. When we omitted PEG from the reaction mixture, the total yield decreased, but soluble and active yields of vtPA were enhanced. This result suggests that a more natural environment may promote protein folding. Spermidine and putrescine naturally occur in *E. coli* and they are known to interact with the ribosome, tRNAs, mRNA and DNA. In the presence of 1.5 mM spermidine and 1.0 mM putrescine and the absence of PEG, the total yield of vtPA was restored and the active vtPA concentration reached 40 µg/mL (FIG. 13).

Effect of the *E. coli* Chaperone, Skp More than 50% of the vtPA produced in the cell-free system was found in the pellet after centrifugation. An examination of production kinetics suggested that this protein aggregation occurred continually during the cell-free reaction. Several *E. coli* proteins exhibit chaperone activity. Since chaperone proteins are used in vivo to guide protein folding and discourage aggregation, we chose to evaluate the *E. coli* periplasmic chaperone, Skp. Skp selectively binds to outer membrane proteins and assists in their folding. Skp binding to folding intermediates of outer membrane proteins improves the target protein solubility and stability and thus decreases the chance of aggregation. In the presence of 300 µg/mL Skp, together with 4 mM GSSG, 1 mM GSH, 75 µg/mL DsbC and with 1 mM IAM cell extract pretreatment, the solubility of vtPA synthesized by the cell-free system was increased by 60–70%. More importantly, the activity of vtPA increased accordingly. The final active yield of vtPA reached approximately 60 µg/mL (FIG. 14). Interestingly, the expression of tPA was also prolonged in the presence of Skp.

Protein synthesis at lower temperature. Protein aggregation appears to be one barrier for producing active multidisulfide bond proteins in the cell-free system. Since it has been reported that lower temperature production can discourage in vivo protein aggregation (Georgiou and Valax, 1996), we also evaluated this for the cell-free system. At 30° C., our system produced 20% more soluble and 10% more active vtPA than at 37° C. in the presence of 4 mM GSSG, 1 mM GSH, 75 µg/mL DsbC, 1.5 mM spermidine, 1.0 mM putrescine and with 1 mM IAM cell extract pretreatment (FIG. 15). Since the total synthesis declined, the percentage solubility increased by 20% at 30° C. and our cell-free system produced approximately 65 µg/mL of active vtPA in a 3 hour reaction. In addition, the reaction could be prolonged at 30° C. and produce more active vtPA.

A relatively oxidized sulfhydryl redox potential is required for production of multiple disulfide bond proteins. Iodoacetamide pretreatment of cell extract provides a stable and oxidized redox for disulfide bond formation and protein folding. With the assistance of isomerase and chaperone activities, the yield of active vtPA was significantly enhanced. A more natural cell-free system omitting PEG and with addition of spermidine and putrescine is beneficial for active vtPA production. And at a lower temperature of reaction, the slower rates of protein synthesis may allow chaperone function to keep pace with the rate of synthesis and thus discourage nascent aggregation.

The helper proteins assisted cell-free system with stable oxidized redox makes it possible to produce vtPA at a large scale. Based on this modified cell-free system, other multiple disulfide bond proteins can also be produced. Compared to in vivo production, a complicated purification or refolding process is not required.

Modifying the physical chemical environment, especially changing the affinity of the components in the cell extract, decreases aggregation. Unlike in vivo expression, conditions of the cell-free reaction can be directly and easily manipulated to provide an optimized environment for the expression of proteins in their native structures, and can easily be used to screen for more efficient isomerases and chaperones for the expression of proteins with disulfide bonds.

What is claimed is:

1. A method for in vitro synthesis of properly folded polypeptides comprising at least one disulfide bond, in a reaction mix comprising a biological extract comprising components of polypeptide synthesis machinery, wherein such components are capable of expressing a nucleic acid encoding a desired polypeptide, the method comprising:
    synthesizing said polypeptide in a reaction mix wherein the biological extract has been pre-treated with a sulfhydryl inactivating agent that irreversibly inactivates free sulfhydryl groups;
    isolating said polypeptide from said reaction mixture, wherein the amount of said polypeptide that is properly folded is enhanced relative to polypeptide synthesized in the absence of pretreatment with said sulfhydryl inactivating agent.

2. The method according to claim 1, wherein said sulfhydryl inactivating agent alkylates free sulfhydryl groups.

3. The method according to claim 1, wherein said sulthydryl inactivating agent is selected from the group consisting of iodoacetamide, N-ethyl maleimides, and iodoacetate.

4. The method according to claim 1, wherein said reaction mix further comprises a redox buffer.

5. The method according to claim 4, wherein said redox buffer comprises one or more of glutathione, dithiothreitol, dithioerythritol, β-mercaptoethanol, thioglycolate and cysteine.

6. The method according to claim 5, wherein said redox buffer comprises a mixture of oxidized and reduced glutathione.

7. The method according to claim 1, wherein said biological extract is a bacterial cell extract from a bacterial cell that has been genetically modified to inactivate one or more reducing enzymes selected from thioredoxin reductase and glutathione reductase.

8. The method according to claim 1, wherein said biological extract is treated to inactivate one or more reducing enzymes selected from thioredoxin reductase and glutathione reductase.

9. The method according to claim 1, wherein said reaction mixture is further modified by the addition of one or more enzymes that enhance polypeptide folding or generation of disulfide bonds.

10. The method according to claim 9, wherein said one or more enzymes that enhance polypeptide folding or generation of disulfide bonds are foldase enzymes and/or chaperonins.

11. The method according to claim 10, wherein said foldase enzyme or chaperonin is selected from the group consisting of RotA (PpiA), FkpA, Skp, SurA, PpiD, DsbA, DsbB, DsbC, DsbD, PDI (protein disulfide isomerase), GroEL/ES, DnaK, DnaJ, GrpE, BIP (immunoglobulin heavy chain binding protein), PPI (peptidylprolyl isomerase) and cyclophilin.

12. The method according to claim 1, wherein said reaction mixture is substantially free of polyethylene glycol.

13. The method according to claim 12, wherein said reaction mixture further comprises one or more of spermine, spermidine and putrescine.

14. The method according to claim 1, wherein said sulfhydryl inactivating agent acetylates free sulfhydryl groups.

15. The method according to claim 1, wherein said sulfhydryl inactivating agent is N-iodoacetyl-N'-(5-sulfo-1-naphthyl)ethylenediamine.

16. A method for optimizing the in vitro synthesis of a properly folded polypeptide comprising at least one disulfide bond, in a plurality of reaction mixtures comprising a biological extract comprising components of polypeptide synthesis machinery, wherein such components are capable of expressing a nucleic acid encoding a desired polypeptide the method comprising:

varying at least one of: the concentration of a foldase or chaperonin, a redox buffer, and temperature, in a plurality of reaction mixtures, wherein the biological extract has been pre-treated with a sulfhydryl inactivating agent that irreversibly inactivates free sulfhydryl groups;

synthesizing said polypeptide in said plurality of reaction mixtures;

quantitating the amount of properly folded polypeptide synthesized in each of said reaction mixtures;

determining which of said plurality of reaction mixtures provides for an optimized yield of properly folded polypeptide.

17. The method according to claim 16, wherein said sulfhydryl inactivating agent alkylates or acetylates free sulfhydryl groups.

18. The method according to claim 17, wherein said redox buffer comprises a mixture of oxidized and reduced glutathione, and said plurality of reaction mixtures varies the ratio of said mixture of oxidized and reduced glutathione.

19. The method according to claim 16, wherein said sulfhydryl inactivating agent is selected from the group consisting of iodoacetamide, N-ethyl maleimides, and iodoacetate, and N-iodoacetyl-N'-(5-sulfo-1-naphthyl)ethylenediamine.

20. The method according to claim 16, wherein said redox buffer comprises one or more of glutathione, dithiothreitol, dithioerythritol, β-mercaptoethanol, thioglycolate and cysteine.

21. The method according to claim 16, wherein said foldase enzyme or chaperonin is selected from the group consisting of RotA (PpiA), FkpA, Skp, SurA, PpiD, DsbA, DsbB, DsbC, DsbD, PDI (protein disulfide isomerase), GroEL/ES, DnaK, DnaJ, GrpE, BIP (immunoglobulin heavy chain binding protein), PPI (peptidylprolyl isomerase) and cyclophilin.

22. The method according to claim 21, wherein said reaction mixture further comprises one or more of spermine, spermidine and putrescine.

23. The method according to claim 16, wherein said reaction mixture is substantially free of polyethylene glycol.

* * * * *